(12) United States Patent
Carson et al.

(10) Patent No.: US 8,695,813 B2
(45) Date of Patent: Apr. 15, 2014

(54) METHOD AND APPARATUS FOR DESOLVATING FLOWING LIQUID

(75) Inventors: William W. Carson, Hopkinton, MA (US); Sidney Bourne, Sudbury, MA (US)

(73) Assignee: Spectra Analysis Instruments, Incorporated, Marlborough, MA (US)

( * ) Notice: Subject to any disclaimer, the term of this patent is extended or adjusted under 35 U.S.C. 154(b) by 650 days.

(21) Appl. No.: 12/312,890

(22) PCT Filed: Dec. 8, 2007

(86) PCT No.: PCT/US2007/025207
§ 371 (c)(1),
(2), (4) Date: May 29, 2009

(87) PCT Pub. No.: WO2008/073361
PCT Pub. Date: Jun. 19, 2008

(65) Prior Publication Data
US 2010/0000943 A1  Jan. 7, 2010

Related U.S. Application Data

(60) Provisional application No. 60/873,848, filed on Dec. 8, 2006, provisional application No. 60/927,646, filed on May 4, 2007.

(51) Int. Cl.
*G01N 30/12* (2006.01)
*G01N 35/10* (2006.01)
*B01D 15/08* (2006.01)
*B01D 45/12* (2006.01)
*H01J 49/00* (2006.01)

(52) U.S. Cl.
USPC ........ 210/512.1; 210/149; 210/151; 210/176; 210/177; 210/180; 210/198.2; 210/188; 250/288; 250/425; 422/70; 422/72; 422/528; 436/45; 436/161; 436/178; 436/181; 73/61.55; 73/61.59

(58) Field of Classification Search
USPC ........ 250/288, 281, 425, 282; 422/54, 70, 72, 422/527, 528, 531, 532, 533; 210/634, 635, 210/640, 656, 739, 742, 741, 774, 787, 788, 210/789, 799, 800, 767, 638, 93, 137, 149, 210/151, 176, 177, 180, 188, 198.2, 243, 210/511, 512.1, 512.3; 159/2.1, 4.01, 6.1, 159/29, 43.1; 73/61.55, 61.59; 436/45, 161, 436/178, 181
See application file for complete search history.

(56) References Cited

U.S. PATENT DOCUMENTS

| | | | |
|---|---|---|---|
| 4,112,297 A * | 9/1978 | Miyagi et al. | 250/288 |
| 4,552,723 A | 11/1985 | Adams et al. | |
| 4,618,769 A | 10/1986 | Johnson et al. | |
| 4,814,612 A | 3/1989 | Vestal et al. | |
| 4,823,009 A | 4/1989 | Biemann et al. | |
| 4,883,958 A | 11/1989 | Vestal | |
| 4,958,529 A | 9/1990 | Vestal | |
| 4,968,885 A * | 11/1990 | Willoughby | 250/288 |
| 4,980,057 A | 12/1990 | Dorn et al. | |
| 5,003,174 A | 3/1991 | Datwyler et al. | |
| 5,039,614 A | 8/1991 | Dekmezian et al. | |
| 5,045,703 A | 9/1991 | Wieboldt et al. | |
| 5,238,653 A | 8/1993 | Bourne | |
| 5,538,643 A | 7/1996 | Kallos et al. | |
| 5,581,081 A | 12/1996 | Kato | |
| 5,772,964 A | 6/1998 | Prevost et al. | |
| 5,901,271 A * | 5/1999 | Benzing et al. | 392/387 |
| 6,177,669 B1 * | 1/2001 | Wells et al. | 250/288 |
| 2003/0189169 A1 | 10/2003 | Wells | |

FOREIGN PATENT DOCUMENTS

| | | |
|---|---|---|
| GB | 2409824 | 7/2005 |
| WO | 0218939 | 3/2002 |

* cited by examiner

*Primary Examiner* — David C Mellon

(74) *Attorney, Agent, or Firm* — David Silverstein; Onello & Mello, LLP

(57) ABSTRACT

Methods and apparatus for desolvating flowing liquid streams while retaining temporal resolution of dissolved substrates are disclosed. A novel small-scale self-regulating spray dryer preserves temporal resolution while desolvating a liquid chromatography eluent stream and depositing the solute onto an optical surface for infrared spectrographic analysis. The liquid eluent is pumped through a heated nebulizer to create a high-speed jet of solute containing liquid and solvent vapor. This jet is directed circumferentially inside a hot cylindrical cavity. Centrifugal force causes the larger liquid droplets to travel along the outer diameter of the cavity. The cavity surface is heated to cause the droplets to film boil. Film boiling reduces droplet contact with the cavity surface thereby retaining the solute in the droplets. The solute temperature is limited by controlling the pressure into which the solvent evaporates from the droplets. When the droplets are sufficiently small, Stokes drag from the exiting solvent vapor carries the droplets out through the center of the cylindrical cavity. After exiting, the superheated solvent vapor further dries the droplets. Solvent vapor is removed by condensation onto a cooled surface. A freezing point reducing agent may be added to improve removal of solvent condensate. Stokes drag from a non-condensable gas maintains the dried droplets in suspension. This suspension travels through an orifice that focuses the impaction of the dried droplets onto the optical surface for infrared analysis. The deposition surface is in an evacuated chamber and is temperature controlled to freeze liquid solutes yet allowing sublimation of residual solvent.

47 Claims, 17 Drawing Sheets

METHOD AND APPARATUS FOR DESOLVATING FLOWING LIQUID

CROSS-REFERENCE TO RELATED APPLICATIONS

This application is a 371 of PCT/US2007/025207, filed Dec. 8, 2007, which claims benefit of the filing dates of U.S. Provisional Application Ser. No. 60/873,848 filed Dec. 8, 2006 and U.S. Provisional Application Ser. No. 60/927,646 filed May 4, 2007.

FIELD OF INVENTION

This invention relates generally to techniques and apparatus for desolvating flowing liquid streams while retaining structural integrity and temporal separation of dissolved solutes. More particularly, this invention relates to apparatus and methods for interfacing liquid chromatography with a Fourier transform infrared spectrometer which is applicable to continuous flow use in normal phase, reverse phase and size exclusion separations.

BACKGROUND OF THE INVENTION

A high degree of compound separation, selectivity and identification is made possible by combining liquid chromatography techniques with molecular detector methods which provide structural information. This approach has been recognized as extremely valuable for the identification of various components of complex chemical mixtures. Particularly, liquid chromatography (LC) has proven to be excellent means for separating a chemical mixture and for determining the individual constituents, either quantitatively or volumetrically. However, LC devices used by themselves have the disadvantage that they do not satisfactorily identify the separated chemical constituents.

On the other hand, the mass spectrometer (MS) is extremely capable and sensitive in identifying single chemical components, but considerable difficulty is experienced in trying to utilize such equipment in identifying the components of a chemical mixture. Consequently, hybrid techniques, which combine chromatography with molecular methods such as mass spectrometry and Fourier transform infrared spectrometry, have been developed and are used extensively for component analysis of complex chemical mixtures.

The high scan speed and sensitivity of Fourier transform infrared (FTIR) spectroscopy have enabled the recording of infrared spectra of individual components of a mixture which have been separated by chromatographic techniques. Coupling of chromatography with FTIR equipment has been successfully accomplished for gas chromatography (GC). However, many chemical compounds and mixtures are not sufficiently volatile for GC separation. Moreover, the sensitivity of a combination GC/FTIR mechanism is reduced for less volatile compounds, making this combination unacceptable. Particularly, the less volatile and/or more polar compounds in a mixture must usually be separated by LC.

Interfacing of LC mechanisms with FTIR devices has not heretofore been substantially successful due to the infrared absorption of the mobile phase of the LC eluent Generally, solvents which are good mobile phases for LC applications are also usually strong infrared absorbers. To try to address this problem, two general types of systems have been developed: (1) flow cells which take advantage of some mobile phases which have large infrared (IR) windows; and (2) elimination of the mobile phase prior to deposition of the eluate on an appropriate substrate. Each of these approaches, however, have their own problems in achieving a reliable and universal interface arrangement.

For example, all solvents absorb some infrared radiation, and the degree of such absorption defines the maximum path length which a flow cell can have which will allow identifiable spectra to be obtained. Additionally, mobile phases having large IR windows are generally of low polarity and are used only for normal-phase LC. The shorter path lengths which must be used to minimize interference resulting from mobile phase absorption similarly limit the volume of the flow cell, thereby limiting the concentration of the analyte being measured at any one instant, and thus compromising the accuracy of the process overall. The major challenge of interfacing normal-phase and reverse-phase LC to IR techniques is the incompatibility of typical solvents to identification of unknown constituents by IR technology. Consequently, water and other typical mobile phases used in LC separations are best eliminated prior to measuring the IR spectrum of a component.

A variety of methods and devices have been directed toward eliminating solvents prior to FTIR procedures, including flowing effluent from a capillary LC column into a stainless steel wire net designed to eliminate the solvent as a result of a heated gas flow. In this approach, the sample material is suspended between the metal meshing, and the deposits are then analyzed. Griffiths et al. developed a system wherein the LC effluent is deposited on an IR transparent substrate as warm nitrogen induces solvent evaporation prior to IR analysis. An interface was developed by Gagel and Biemann in which deposition of the sample material was to be continuous and where effluent from a microbore LC was continuously sprayed onto a rotating disk as warm nitrogen was passed across the disk to evaporate the solvent. In that procedure, however, the FTIR spectra were measured off-line by fastening the collection device to a reflectance accessory.

A solvent removal interface developed by Kalasinsky for reverse phase LC contemplated the elimination of water by employing a particular chemical (2,2'-dimethoxypropane) to convert the water to methanol and acetone for deposition on a KCl substrate. Such conversion requires specific matching of chemicals and collection substrates, and does not truly remove the solvent but merely converts it to other substances which can independently add interference to analysis results.

Browner and coworkers developed a monodisperse aerosol generator interface for combining LC and FTIR spectrometry known as the MAGIC interface. With this interface, mobile phase elimination was to be accomplished at room temperature, wherein effluent from an LC enters the interface through a 25 micrometer diameter orifice to form a liquid jet. The jet is dispersed by a Helium (He) stream to create a fine aerosol which is directed from a desolvation chamber into first and second momentum separators. In the first momentum separator, evaporated solvent and Helium are removed by vacuum pumps, and the nonvolatile analyte continues into the second momentum separator where any residual volatile material is to be removed. The nonvolatile analyte is then deposited on a KBr (potassium bromide) window which is removed and placed in a beam condenser for IR analysis. Because the solvent is eliminated prior to deposition on the substrate, the isolated analyte can be deposited on a variety of substrates for various IR detection methods.

In U.S. Pat. Nos. 4,814,612 and 4,883,958, which are incorporated herein by reference, M. L. Vestal et al. described similar apparatuses and methods for coupling LC and solid phase detectors, including the use of thermospray vaporizers which vaporize most of the solvent prior to introduction to a desolvation chamber. The device described in the Vestal '958 patent further contemplates passing the vaporized solvent and added carrier gas through one or more solvent removal chambers, which can remove solvent by condensation or diffusion through a membrane to a counterflowing gas stream. This device may further include a momentum separator to concentrate particles relative to the remaining solvent vapor and carrier gas. This patent also teaches the direction of a particle beam for impact with a cryogenically cooled deposition surface. In the Vestal '612 patent, a moving belt is provided for receiving the particle beam, and a temperature transducer is positioned adjacent the belt to maintain the belt at a temperature where no significant amount of the particle sample will be vaporized, yet warm enough that residual liquid solvent is vaporized efficiently in a stream of counterflowing gas which passes over the belt.

The Vestec Universal Interface incorporates many of the features described in the Vestal patents mentioned above, and was commercially available in the industry from Vestec Corporation of Houston, Tex.

An apparatus combining LC technology with mass spectrometry is described in U.S. Pat. No. 4,980,057, which is incorporated herein by reference, issued to S. B. Dorn, et al. The Dorn '057 device includes a nebulizer which volatilizes the LC eluate to form an aerosol which passes through a desolvation chamber. The nebulizer introduces an inert gas which helps vaporize the solvent and carries the aerosol to a momentum separator which accelerates the particles to sonic velocities. The momentum separator includes three vacuum pumping stages, wherein the first two stages are defined by conical skimmer nozzles, and the third chamber includes a long inlet tube which provides the vacuum pumping restriction. The resulting particle beam is provided to the MS ion source for analysis.

Another approach to this analysis problem is the LC-IR sample delivery system developed by S. Bourne based on ultrasonic nebulization followed by evaporation Versions of this system have been available from Bourne Scientific, Nicolet and Bio-Rad corporations, as described in U.S. Pat. Nos. 5,045,703; 5,039,614; 5,238,653 and 4,552,723, which are incorporated herein by reference.

LC sample delivery by pneumatic, thermal or ultrasonic nebulization, followed by evaporation and deposition at atmospheric pressure or in a vacuum onto a rotating germanium disk is a technique developed by Lab Connections. The germanium disk is then transferred to, and read by an FTIR, as described in U.S. Pat. Nos. 5,772,964 and 4,823,009, which are incorporated herein by reference.

In U.S. Pat. No. 5,538,643, which is incorporated herein by reference, Kallos describes an LC-FTIR interface sample handling process consisting of nebulizing an LC elulent, removing the solvent by a combination membrane-and-momentum separator, followed by focused deposition onto a cryogenic surface with subsequent thermal manipulation of this surface to remove remaining solvent.

Consequently, while a great number of investigations and techniques have been attempted heretofore, LC/FTIR interfaces have thus far shown only limited success in providing interpretable IR spectra from normal-phase and reverse-phase separations, due to inadequate solvent elimination and/or limited applicability to IR analysis. Although many of these previously developed systems generate aerosols from the liquid stream, and partially desolvate the stream, none of them effectively, reliably and robustly separates the solvent vapor and non-condensable carrier gas from the particulate stream.

These and other deficiencies in or limitations of the prior art are overcome in whole or at least in part by the apparatus and related methods of this invention. As described hereinafter, the present invention successfully and effectively removes interfering materials, thus enabling applications of the particle stream, such as for analysis, which would otherwise be prevented or limited.

OBJECTS OF THE INVENTION

Accordingly, it is a principal object of this invention to provide improved treatment techniques and apparatus for desolvating flowing liquid streams containing one or more solutes while retaining the chemical and structural integrity and temporal separation of such solutes.

A specific object of the present invention is to provide methods and apparatus to continuously remove the solvents from a fluid mixture comprising liquid components and solute components and deposit the resolved, concentrated, structurally integral solutes on a surface for subsequent infrared absorption analysis.

SUMMARY OF THE INVENTION

In general, methods and apparatus of the present invention consist of a series of process steps or stages, and related apparatus components, that comprise a novel spray drier system for processing a flowing liquid stream containing low-volatility components by removing the liquid solvent component and leaving the low-volatility solute components. The spray drier system of this invention preserves the chemical and structural integrity, as well as the temporal resolution, of the low volatility components (the solutes) while desolvating the liquid stream. The dried solute may be further processed, deposited onto a solid surface, or collected as a solid, powder or liquid. In one preferred embodiment, the liquid stream is a chromatographic effluent and the dried solute is deposited as a small spot or stripe on a surface for infrared spectrographic analysis. The term "solute" as used in this disclosure is hereby defined as and intended to include dispersed and suspended, as well as dissolved, solids and relatively low vapor pressure liquids.

The novel spray drier system of this invention comprises in part a nebulizer which converts the liquid stream into a high speed aerosol jet which can then be directed circumferentially around the inside surface of a hot, generally cylindrical cavity of a chamber. As used herein, the term "aerosol" is hereby defined to include liquid droplets and/or solid particles suspended or entrained in a gas-phase fluid. Centrifugal force, which can be provided by the jet velocity, causes the larger liquid droplets to travel along the outer diameter of the cavity. The cavity inner surface is heated to a temperature of at least 20° C., preferably at least 50° C., more preferably at least 100° C., above the boiling point of the liquid component of the fluid stream, to cause the droplets approaching that surface to "film boil." Film boiling rapidly evaporates solvent from the droplets. In film boiling, the rapid release of freshly evaporated solvent vapor creates a gas layer adjacent the heated surface that prevents droplet contact with the cavity wall, thereby retaining the solute in the droplets. To ensure that the phenomenon of "film boiling" occurs in the chamber cavity, the heated inner surface of the cavity should be maintained at a temperature that is at least 20° C., preferably at least 50° C., and more preferably at least 100° C., hotter than the boiling point of the liquid component of the fluid stream being treated. The solute is protected from thermal damage by the combination of a short residence time and by being inside the droplet, which is cooled by solvent evaporation.

When the droplets have evaporated to a sufficiently small size, Stokes drag forces from the exiting solvent vapor will exceed the centrifugal force and carry the droplets out of the chamber, for example along the central axis of the cylindrical cavity. For convenience, the term "cyclone" will be used herein for the chamber/cylindrical cavity assembly as described above. After the droplets leave the cyclone inner surface, heat exchange with the superheated solvent vapor further dries the droplets. If not already present, a small amount of non-condensable gas may be added. This added gas helps to maintain the dried droplets in an aerosol suspension during and after the removal of solvent vapor. Solvent vapor is removed by condensation onto a cooled surface in a first-stage condenser unit Operating this first-stage condenser unit above the freezing point of the solvent produces a liquid condensate that can be continuously drained. The amount of remaining solvent vapor may be further reduced by an optional second condenser stage operated at a lower temperature than the first-stage condenser unit A solvent freeze point reducing agent, such as methanol, may be added to the second condenser stage. For a preferred chromatographic application, the dried droplet aerosol suspension flows through an orifice that focuses the dried droplets into a narrow beam. An optical surface is placed under the beam to collect the solute. The deposition surface is typically positioned in an evacuated chamber and is temperature controlled to condense or freeze liquid solutes while preventing condensation or allowing sublimation of any residual solvent. To prevent "bouncing" of the dried particle off of the optical surface, a solvent or other adhesion-improving agent may be added to the deposition region. The optical surface is then moved into the focus of the infrared microscope beam for analysis of the solute collected on the surface.

The following discussion is intended to convey the inventors' present understanding concerning how this invention operates, but such discussion should not be interpreted to limit the validity or scope of the claims. Much of the uniqueness and advantage of the cyclone apparatus of this invention is its ability to accept a wide range of starting droplet sizes, and to automatically by virtue of its operation deliver only enough heat to each droplet as needed to evaporate the predominant portion of the solvent in each droplet Evaporative cooling effects with this apparatus limit the maximum droplet temperature to roughly the solvent boiling point at the cyclone operating pressure. Each individual droplet remains in the cyclone only long enough to shrink to a relatively uniform and very small size. Because the residence time of a droplet in the cyclone is inversely related to the staring droplet size, the result is minimal exposure of each droplet to high temperature, potentially thermally degrading or volatile-solute evaporating conditions. The balance between opposing centrifugal force and the drag forces within the cyclone from the exiting solvent vapor determines what that droplet size will be. The concentrated droplets are removed from proximity to the cyclone surface while they still contain a relatively small amount of solvent. Because the exiting droplets have a relatively narrow homogeneous size distribution, the amount of additional heat required to thereafter complete the evaporative removal of residual solvent is similar for each droplet Heat transfer from the super heated solvent vapor in this system provides this relatively uniform additional amount of heat to effectively complete the evaporation process. At the same time evaporation of this residual solvent continues to protect the sample (solute) for most of this drying step. Because the droplets are already leaving the cyclone before they can reach full dryness, the duration of droplet exposure to conditions without evaporative cooling protection is minimal thereby minimizing opportunities for thermal degradation of the sample.

Unlike most prior art processes in this field, the cyclone of this invention evaporates the solvent without the addition of, and dilution by, a drying gas. In most prior art techniques in this field, the problem of supplying sufficient heat to complete evaporation has required either: (1) a large mass of drying gas; (2) a very long residence time to allow a low temperature differential to transfer sufficient heat through the gas to the liquid; (3) exposure of the sample to excessively high temperatures; or (4) a combination of these approaches. Worst of all, in the prior art, is the duration of exposure of all the solute to these drying conditions for the relatively long time needed to dry the largest of the droplets. All smaller droplets are thereby exposed to excessive drying conditions that the present invention avoids. By contrast, the methods and apparatus of this invention do not require any of these prior art drying techniques and thereby avoid the associated disadvantages.

As will be apparent from the following description, the methods and apparatus of this invention may be practiced in a number of different ways, all of which are considered to be within the scope of the invention. At the present time, it is envisioned that there will be certain preferred embodiments, especially in connection with liquid chromatography. Among such preferred invention embodiments are the following:

(1) Apparatus for evaporating liquid from an inlet fluid stream comprising liquid and solute components, said apparatus comprising in combination:
    (a) a chamber having a chamber cavity with upper and lower regions and defined in part by a generally cylindrical-shaped cavity side wall defining a chamber axis;
    (b) a source of heat that heats the cavity side wall sufficiently to maintain the temperature of the cavity side wall at least 20° C. greater than the boiling point of the liquid component of a fluid stream in the chamber cavity at the operating pressure inside the chamber cavity;
    (c) a fluid stream chamber inlet extending from outside the chamber into the upper region of the chamber cavity;
    (d) a fluid vertical direction imparting element in or associated with said chamber cavity, said element acting to impart a rotational direction to an inlet fluid stream introduced into said chamber cavity; and,
    (e) a chamber outlet extending from the lower region of the chamber cavity to outside the chamber.

(2) An apparatus according to paragraph (1) above wherein said fluid vortical direction imparting element is selected from the group consisting of: (i) a fluid inlet that directs an inlet fluid stream so as to have a net tangential component relative to the cylindrical-shaped cavity side wall; (ii) a rotating element in said chamber cavity on which an inlet fluid stream impinges and at least a portion of which fluid stream is thereby directed outwards toward the cavity side wall with a net circumferential directional component; (iii) a source of moving gas in said chamber cavity that imparts motion having a net circumferential component to an inlet fluid stream; and, (iv) a rotational device that rotates the chamber cavity.

(3) An apparatus according to paragraph (I) above wherein the source of heat that heats the cavity side wall is selected from the group consisting of: (i) an electric resistance heater; (ii) an electric cartridge heater; (iii) a surface mounted electric resistance heater; (iv) a deposited film electrically conductive resistance heater; (v) an electrically conductive heater deposited on the cylindrical-shaped surface; (vi) a radio frequency electrical induction heater; (vii) a microwave heater; (viii) a flame; (ix) an infrared radiant heater; (x) a high temperature gas; and, (xi) a high temperature liquid.

(4) An apparatus according to paragraph (1) above wherein said fluid vortical direction imparting element is capable of causing an inlet fluid stream to rotate within the chamber cavity at a sufficient velocity to maintain the fluid stream traveling substantially circumferentially adjacent said cylindrical-shaped cavity side wall.

(5) An apparatus according to paragraph (1) above wherein said source of heat heats the cavity side wall to a temperature high enough to establish and maintain film boiling of the fluid stream adjacent said cavity side wall.

(6) An apparatus according to paragraph (1) above wherein the chamber outlet is located in said lower region of the chamber cavity such that a fluid stream leaving the chamber through the chamber outlet must pass through a region that is closer to the chamber axis than to the cavity side wall.

(7) An apparatus according to paragraph (1) above wherein the chamber forms a sealed enclosure capable of operating at a pressure different than the surrounding environment.

(8) An apparatus according to paragraph (I) above wherein film boiling prevents the fluid stream from contacting the cavity side wall and the apparatus operates without leaving any substantial portion of the solute component on the cavity side wall.

(9) An apparatus according to paragraph (1) above further comprising a fluid stream in said chamber cavity wherein the inlet fluid stream is an aerosol stream containing discrete liquid droplets.

(10) An apparatus according to paragraph (1) above wherein the liquid portion of a fluid stream exiting the chamber cavity has a concentration of solute that is at least ten times the concentration of solute in the inlet fluid stream.

(11) An apparatus according to paragraph (1) above wherein the inlet fluid stream is caused to rotate within the chamber cavity by its inlet velocity and the orientation of the fluid stream chamber inlet.

(12) An apparatus according to paragraph (1) above wherein the inlet fluid stream is caused to rotate within the chamber cavity by being impacted by a stream of solvent vapor, other liquid vapor, other gas, sample-containing liquid, other liquid, liquid droplets or a combination thereof (13) An apparatus according to paragraph (1) above further comprising a conduit that connects an outlet of a liquid chromatograph to the fluid stream chamber inlet.

(14) An apparatus according to paragraph (1) above further comprising a conduit that directs concentrated solute droplets or substantially dry particles coming from the chamber outlet directly or via another treatment component, such as a reactor, to a light scattering detector, optical absorbance analyzer, infrared spectrometer, mass spectrometer, nuclear magnetic resonance spectrometer, atomic emission spectrometer, atomic absorbance spectrometer or flame ionization detector.

(15) Apparatus for converting a fluid steam comprising liquid and solute components into a nebulized stream comprising gas, vapor and/or aerosol, said apparatus comprising in combination:
  a. a small diameter, very thin-walled capillary tube comprising an electrically conductive material, said tube having a capillary tube fluid entrance end and a capillary tube fluid discharge end; and, b. a source of heat for heating the capillary tube, said source of heat comprising an electric current source and electrical connections between the current source and the respective ends of the capillary tube for passing electrical current through the capillary tube, said source of heat providing sufficient heat such that a fluid stream passing from the capillary tube entrance end to the capillary tube discharge end is heated to a superheated temperature that is at least 20° C. above the boiling point of the liquid component at the capillary tube discharge end pressure.

(16) An apparatus according to paragraph (15) above further comprising an electrical resistance measuring device connected between the respective ends of the capillary tube for generating an output to assess the sufficiency of the heat supplied to the capillary tube.

(17) An apparatus according to paragraph (16) above further comprising a control mechanism electrically connected to the electrical resistance measuring device, whereby the control mechanism regulates the electrical supply from the electric current source in accordance with the output generated by the electrical resistance measuring device in order to maintain the capillary tube at a sufficiently high average temperature along its length to produce a nebulized steam at the capillary tube discharge end.

(18) An apparatus according to paragraph (15) above wherein the capillary tube has a length of about 1 to 20 cm and an inside diameter of about 0.05 to 0.2 mm.

(19) An apparatus according to paragraph (15) above wherein the thermal mass of the capillary tube is less than 5 times that of a liquid inside the capillary tube.

(20) An apparatus according to paragraph (15) above further comprising an electric power control mechanism which senses a need for a change in the electric power being delivered to the capillary tube and substantially effects such an adjustment in a time of 100 milliseconds or less.

(21) A system for generating and desolvating a nebulized fluid stream wherein a nebulized fluid stream emerging from the capillary tube discharge end of the capillary tube according to paragraph (15) above is sent to a fluid stream inlet of an evaporating apparatus for evaporating liquid from the nebulized fluid stream, said evaporating apparatus comprising in combination:

a. a chamber having a chamber cavity with upper and lower regions and defined in part by a generally cylindrical-shaped cavity side wall defining a chamber axis;

b. a source of heat that heats the cavity side wall sufficiently to maintain the temperature of the cavity side wall at least 20° C. greater than the boiling point of the liquid component of a fluid stream in the chamber cavity at the operating pressure inside the chamber cavity;

c. a fluid stream chamber inlet extending from outside the chamber into the upper region of the chamber cavity;

d. a fluid vortical direction imparting element in or associated with said chamber cavity, said element acting to impart a rotational direction to an inlet fluid stream introduced into said chamber cavity; and, e. a chamber outlet extending from the lower region of the chamber cavity to outside the chamber.

(22) A system for separating liquid from a fluid stream comprising liquid and solute components, said system comprising an evaporation apparatus according to paragraph (1) above in combination with a condenser apparatus, wherein the condenser apparatus comprises:

a. a condenser region defined by a condenser fluid entrance in fluid communication with the chamber outlet of the evaporation apparatus, a condenser discharge end, and a condenser flow path between the condenser fluid entrance and the condenser discharge end, said condenser flow path including at least a condenser surface; and, b. a source of providing cooling to a fluid stream flowing along the condenser flow path, said cooling being sufficient to cool the fluid stream to a temperature below the condensation temperature of a condensable gas component of the fluid stream prior to reaching the condenser discharge end.

(23) A system according to paragraph (22) above wherein said condenser surface is cooled to condense the condensable gas component.

(24) A system according to paragraph (22) above wherein said condenser region comprises the interior of a condenser tube, the outside of which is in direct or indirect contact with a cooling fluid at a temperature low enough to provide the required cooling effect.

(25) A system according to paragraph (22) above wherein said source of providing cooling comprises air cooling followed by Peltier cooling.

(26) A system according to paragraph (22) above wherein the condenser apparatus comprises a single-stage condenser.

(27) A system according to paragraph (22) above wherein the condenser apparatus comprises a multi-stage condenser.

(28) A system according to paragraph (21) above further comprising a condenser apparatus wherein the condenser apparatus comprises:
   a. a condenser region defined by a condenser fluid entrance in fluid communication with the chamber outlet of the evaporation apparatus a condenser discharge end, and a condenser flow path between the condenser fluid entrance and the condenser discharge end, said condenser flow path including at least a condenser surface; and,
   b. a source of providing cooling to a fluid stream flowing along the condenser flow path, said cooling being sufficient to cool the fluid stream to a temperature below the condensation temperature of a condensable gas component of the fluid stream prior to reaching the condenser discharge end.

(29) A system for generating and desolvating a fluid stream comprising liquid and solute components, said system comprising in combination:
   a. a small diameter, very thin-walled capillary tube comprising an electrically conductive material, said tube having a capillary tube fluid entrance end and a capillary tube fluid discharge end;
   b. a source of heat for heating the capillary tube, said source of heat comprising an electric current source and electrical connections between the current source and the respective ends of the capillary tube for passing electrical current through the capillary tube, said source of heat providing sufficient heat such that a fluid stream passing from the capillary tube entrance end to the capillary tube discharge end is heated to a superheated temperature that is at least 20° C. above the boiling point of the liquid component at the capillary tube discharge end pressure;
   c. a chamber having a chamber cavity with upper and lower regions and defined in part by a generally cylindrical-shaped cavity side wall defining a chamber axis, said chamber further comprising a fluid stream chamber inlet extending from outside the chamber into the upper region of the chamber cavity wherein said chamber inlet is in fluid communication with the capillary tube fluid discharge end;
   d. a source of heat that heats the cavity side wall sufficiently to maintain the temperature of the cavity side wall at least 20° C. greater than the boiling point of the liquid component of a fluid stream in the chamber cavity at the operating pressure inside the chamber cavity;
   e. a fluid vortical direction imparting element in or associated with said chamber cavity, said element acting to impart a rotational direction to an inlet fluid stream introduced into said chamber cavity; and,
   f. a chamber outlet extending from the lower region of the chamber cavity to outside the chamber.

(30) A system for separating liquid from a fluid stream comprising liquid and solute components, said system comprising in combination:
   a. a chamber having a chamber cavity with upper and lower regions and defined in part by a generally cylindrical-shaped cavity side wall defining a chamber axis;
   b. a source of heat that heats the cavity side wall sufficiently to maintain the temperature of the cavity side wall at least 20° C. greater than the boiling point of the liquid component of a fluid stream in the chamber cavity at the operating pressure inside the chamber cavity;
   c. a fluid stream chamber inlet extending from outside the chamber into the upper region of the chamber cavity;
   d. a fluid vortical direction imparting element in or associated with said chamber cavity, said element acting to impart a rotational direction to an inlet fluid stream introduced into said chamber cavity;
   e. a chamber outlet extending from the lower region of the chamber cavity to outside the chamber,
   f. a condenser region defined by a condenser fluid entrance in fluid communication with the chamber outlet, a condenser discharge end, and a condenser flow path between the condenser fluid entrance and the condenser discharge end, said condenser flow path including at least a condenser surface; and,
   g. a source of providing cooling to a fluid stream flowing along the condenser flow path, said cooling being sufficient to cool the fluid stream to a temperature below the condensation temperature of a condensable gas component of the fluid stream prior to reaching the condenser discharge end.

(31) A system for generating and desolvating a fluid stream comprising liquid and solute components, said system comprising in combination:
   a. a small diameter, very thin-walled capillary tube comprising an electrically conductive material, said tube having a capillary tube fluid entrance end and a capillary tube fluid discharge end;
   b. a source of heat for heating the capillary tube, said source of heat comprising an electric current source and electrical connections between the current source and the respective ends of the capillary tube for passing electrical current through the capillary tube, said source of heat providing sufficient heat such that a fluid stream passing from the capillary tube entrance end to the capillary tube discharge end is heated to a superheated temperature that is at least 20° C. above the boiling point of the liquid component at the capillary tube discharge end pressure;
   c. a chamber having a chamber cavity with upper and lower regions and defined in part by a generally cylindrical-shaped cavity side wall defining a chamber aids, said chamber further comprising a fluid stream chamber inlet extending from outside the chamber into the upper region of the chamber cavity wherein said chamber inlet is in fluid communication with the capillary tube fluid discharge end;
   d. a source of heat that heats the cavity side wall sufficiently to maintain the temperature of the cavity side wall at least 20° C. greater than the boiling point of the liquid component of a fluid stream in the chamber cavity at the operating pressure inside the chamber cavity;
   e. a fluid vortical direction imparting element in or associated with said chamber cavity, said element acting to impart a rotational direction to an inlet fluid stream introduced into said chamber cavity;

f. a chamber outlet extending from the lower region of the chamber cavity to outside the chamber;

g. a condenser region defined by a condenser fluid entrance in fluid communication with the chamber outlet, a condenser discharge end, and a condenser flow path between the condenser fluid entrance and the condenser discharge end, said condenser flow path including at least a condenser surface; and, h. a source of providing cooling to a fluid stream flowing along the condenser flow path, said cooling being sufficient to cool the fluid stream to a temperature below the condensation temperature of a condensable gas component of the fluid stream prior to reaching the condenser discharge end.

(32) A method for evaporating liquid from an inlet fluid stream comprising liquid and solute components, said method comprising the steps of:

a. a introducing an inlet fluid stream into the upper portion of a cyclone region defined by a generally cylindrical-shaped cyclone side wall;

b. imparting a rotational direction to the inlet fluid steam that causes the fluid stream to circulate circumferentially within the cylindrical-shaped cyclone side wall;

c. maintaining the cyclone side wall at a temperature at least 20° C. greater than the boiling point of the liquid component of the fluid stream; and, d. producing at a lower portion of the cyclone region a fluid stream in which the concentration of solute is significantly greater than the concentration of solute in the inlet fluid stream.

(33) The method according to paragraph (32) above wherein the step of imparting a rotational direction to the inlet fluid stream is effected by: (i) a fluid inlet that directs an inlet fluid stream so as to have a net tangential component relative to the cylindrical-shaped cavity side wall; (ii) a rotating element in said chamber cavity on which an inlet fluid stream impinges and at least a portion of which fluid stream is thereby directed outwards toward the cavity side wall with a net circumferential directional component; (iii) a source of moving gas in said chamber cavity that imparts motion having a net circumferential component to an inlet fluid stream; or, (iv) a rotational device that rotates the chamber cavity.

(34) The method according to paragraph (32) above wherein the step of maintaining the cyclone side wall at a suitable temperature is effected by a heating element selected from the group consisting of: (i) an electric resistance heater; (ii) an electric cartridge heater; (iii) a surface mounted electric resistance heater; (iv) a deposited film electrically conductive resistance heater; (v) an electrically conductive heater deposited on the cylindrical-shaped surface; (vi) a radio frequency electrical induction heater; (vii) a microwave heater; (viii) a flame; (ix) an infrared radiant heater; (x) a high temperature gas; and, (xi) a high temperature liquid.

(35) The method according to paragraph (32) above wherein the step of imparting a rotational direction to the inlet fluid stream causes the inlet fluid stream to rotate within the cyclone side wall at a sufficient velocity to maintain the fluid stream traveling substantially circumferentially adjacent said cyclone side wall.

(36) The method according to paragraph (32) above wherein the cyclone side wall is maintained at a temperature high enough to establish and maintain film boiling of the fluid stream adjacent the cyclone side wall.

(37) The method according to paragraph (32) above further comprising the step of having a fluid stream with an elevated concentration of solute leave the lower portion of the cyclone region through an outlet that is closer to an axis of the cyclone region than it is to the cyclone side wall.

(38) The method according to paragraph (32) above wherein said inlet fluid stream is an aerosol containing discrete liquid droplets.

(39) The method according to paragraph (32) above wherein the liquid portion of a fluid stream exiting the lower portion of the cyclone region has a concentration of solute that is at least ten times the concentration of solute in the inlet fluid stream.

(40) The method according to paragraph (32) above wherein the inlet fluid stream comes from the outlet of a liquid chromatograph.

(41) The method according to paragraph (32) above wherein a fluid stream exiting the lower portion of the cyclone region is sent directly, or via another treatment component, to a light scattering detector, optical absorbance analyzer, infrared spectrometer, mass spectrometer, nuclear magnetic resonance spectrometer, atomic emission spectrometer, atomic absorbance spectrometer or flame ionization detector.

(42) A method for converting a fluid stream comprising liquid and solute components into a nebulized stream comprising gas, vapor and/or aerosol, said method comprising the steps of:

(a) passing the fluid stream though the interior of a small diameter, very thin-walled capillary tube comprising an electrically conductive material; and, (b) heating the capillary tube by passing an electric current through the capillary tube sufficient to heat the fluid stream before it reaches the capillary tube discharge end of the capillary tube to a superheated temperature that is at least 20° C. above the boiling point of the liquid component of the fluid stream.

(43) The method according to paragraph (42) above further comprising the step of regulating the electrical power supply to the capillary tube based on a measurement of the electrical resistance of the capillary tube.

(44) A method for generating and desolvating a nebulized fluid stream comprising the steps of (a) passing a fluid stream processed in accordance with the method of paragraph (42) above from the discharge end of the capillary tube into the upper portion of a cyclone region defined by a generally cylindrical-shaped cyclone side wall;

(b) imparting a rotational direction to the fluid stream in the cyclone region that causes the fluid stream to circulate circumferentially within the cylindrical-shaped cyclone side wall;

(c) maintaining the cyclone side wall at a temperature at least 20° C. greater than the boiling point of the liquid component of the fluid stream; and, (d) producing at a lower portion of the cyclone region a fluid stream in which the concentration of solute is significantly greater than the concentration of solute in the fluid stream that was introduced into the upper portion of the cyclone region.

(45) A method for separating liquid from a fluid stream comprising liquid and solute components, said method comprising the steps of:

(a) recovering a concentrated fluid stream processed in accordance with the method of paragraph (32) above from the lower portion of the cyclone region; and, (b) cooling the concentrated fluid stream to a temperature below the condensation temperature of a condensable gas component of the concentrated fluid stream.

(46) A method according to paragraph (44) above further comprising the steps of:

(a) recovering a concentrated fluid stream from the lower portion of the cyclone region; and, (b) cooling the concentrated fluid stream to a temperature below the condensation temperature of a condensable gas component of the concentrated fluid stream.

(47) A method for generating and desolvating a nebulized fluid stream, said method comprising the steps of:

(a) passing a fluid stream through the interior of a small diameter, very thin-walled capillary tube comprising an electrically conductive material;

(b) heating the capillary tube by passing an electric current through the capillary tube sufficient to heat the fluid stream before it reaches the capillary tube discharge end of the capillary tube to a superheated temperature that is at least 20° C. above the boiling point of the liquid component of the fluid stream;

(c) passing the fluid stream coming from the capillary tube discharge end of the capillary tube into the upper portion of a cyclone region defined by a generally cylindrical-shaped cyclone side wall;

(d) imparting a rotational direction to the fluid stream inside the cyclone region that causes the fluid stream to circulate circumferentially within the cylindrical-shaped cyclone side wall;

(e) maintaining the cyclone side wall at a temperature at least 20° C. greater than the boiling point of the liquid component of the fluid stream; and, (f) producing at a lower portion of the cyclone region a fluid stream in which the concentration of solute is significantly greater than the concentration of solute in the fluid stream introduced into the upper portion of the cyclone region.

(48) A method for separating liquid from a fluid stream comprising liquid and solute components, said method comprising the steps of (a) passing the fluid stream through the interior of a small diameter, very thin-walled capillary tube comprising an electrically conductive material;

(b) heating the capillary tube by passing an electric current through the capillary tube sufficient to heat the fluid stream before it reaches the capillary tube discharge end of the capillary tube to a superheated temperature that is at least 20° C. above the boiling point of the liquid component of the fluid stream;

(c) passing the fluid stream coming from the capillary tube discharge end of the capillary tube into the upper portion of a cyclone region defined by a generally cylindrical-shaped cyclone side wall;

(d) imparting a rotational direction to the fluid stream in side the cyclone region that causes the fluid stream to circulate circumferentially within the cylindrical-shaped cyclone side wall;

(e) maintaining the cyclone side wall at a temperature at least 20° C. greater than the boiling point of the liquid component of the fluid stream;

(f) producing at a lower portion of the cyclone region a concentrated fluid steam in which the concentration of solute is significantly greater than the concentration of solute in the fluid stream introduced into the upper portion of the cyclone region; and, (g) withdrawing said concentrated fluid stream from the lower portion of the cyclone region and cooling the concentrated fluid stream to a temperature below the condensation temperature of a condensable gas component of the concentrated fluid stream.

In some applications of this invention, the low-volatility components will be temporally and spatially separated from each other in the same relation as they were in the original untreated stream. The fluid stream may, for example, consist essentially of a liquid solvent that may change in composition as treatment in accordance with this invention progresses. The fluid stream may carry a variety of dissolved and/or dispersed solid and/or liquid components, each of which is typically carried in a short section of the stream, frequently as the only dissolved component in that section. The solvent portion of the stream may be comprised of any suitable liquid.

Among other applications, this invention may specifically be applied to treating the eluate from a high-pressure liquid chromatograph instrument, with typical liquid flow rates ranging from about 0.1 to 2 ml per minute. AU of such LC eluate may be processed according to the present invention. Alternatively, a portion of such LC eluate may be treated in accordance with this invention, while another portion may be directed to another instrument, such as a mass spectrometer, or collected for other purposes, or not utilized at all. In a typical liquid chromatography application, the liquid consists essentially of organic solvents, or water mixed with a varying concentration of one or more miscible organic solvents, and may additionally contain varying concentrations of one or more additives. The water, organic solvents, and volatile additives, if present, can all be substantially removed or separated from the low-volatility components by the methods and apparatus of this invention.

This invention is based on the principle that a flowing fluid stream can be treated according to the invention to produce a treated flowing gas stream that carries the originally dissolved components (solutes) as particulate matter, but at a mass concentration substantially higher, e.g., a 10 fold increase in concentration, than that in the original fluid stream. The invention thus enables further processing of the particulate stream, especially types of processing that would be rendered difficult or impossible by the continued presence of the liquid. One example of such further processing which is facilitated by this invention involves directing the particulate stream onto a window or another optically transparent or translucent surface or onto a porous surface such as a porous membrane, where the particulate matter collects in a configuration which is favorable for observation, for example by an infrared spectrometer using microscope optics. Another example of such further processing that is facilitated by this invention involves directing the particulate stream through a reaction chamber, and thence into a detector designed for gas chromatography, thus allowing the application of gas chromatography detectors to liquid chromatography eluents.

In alternate embodiments, this invention may also be used for other applications outside of this liquid flow rate range or where maintaining temporal separation of solute components is not important. In applications of this invention that are unrelated to chromatography, temporal resolution may not be important, such as in small scale and general-purpose spray drying of specialty chemicals, foods or other dissolved or suspended materials.

These and other benefits, advantages and applications for the methods and apparatus of this invention will be better understood by the following detailed description and the accompanying drawings.

DESCRIPTION OF PREFERRED EMBODIMENTS

Figure 2:
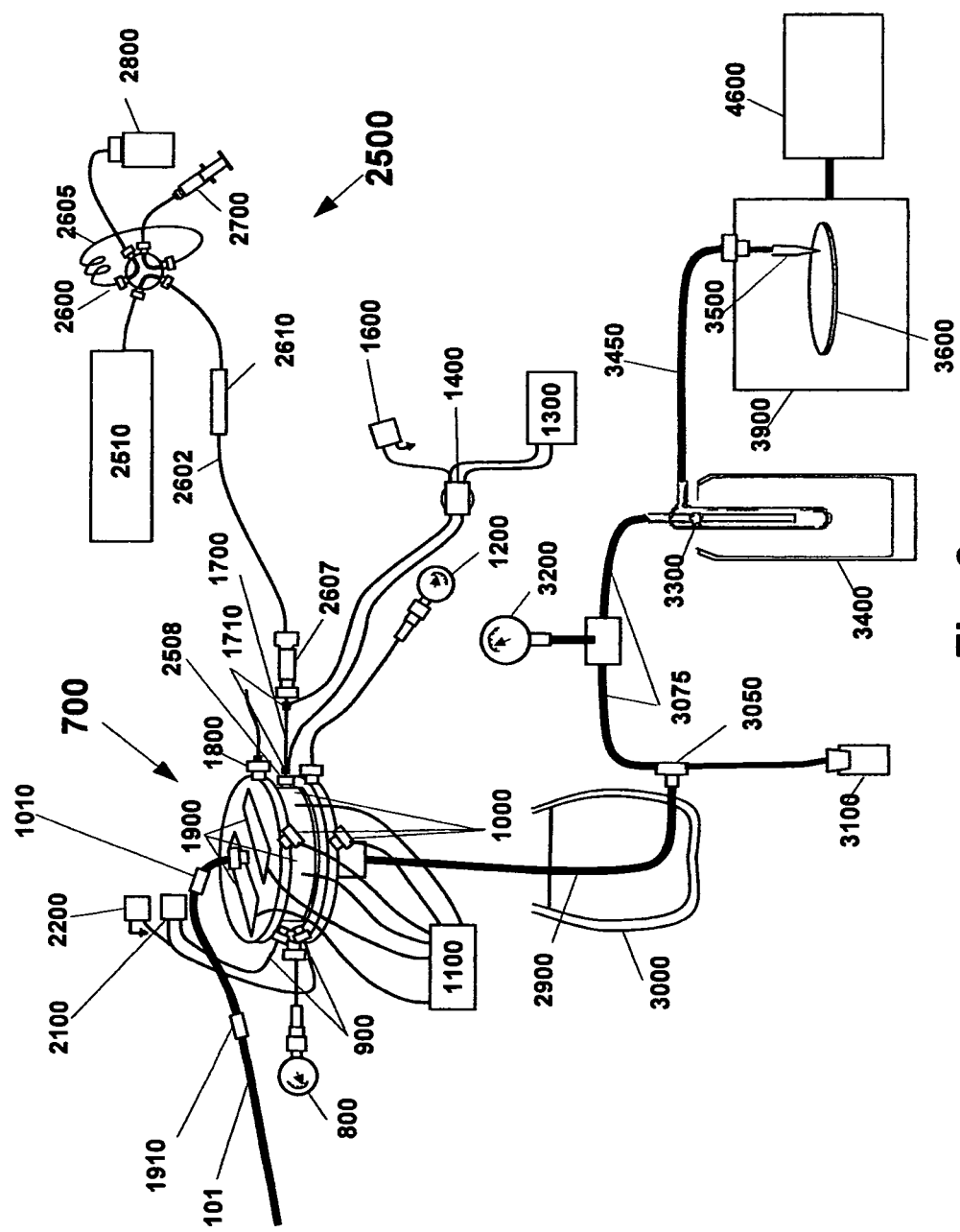
FIG. 2 is a schematic illustration of an apparatus for desolvation of a flowing stream according to an embodiment of the present invention.

The present invention discloses methods and apparatus as schematically illustrated in FIG. 2, which illustrates a simplified version of an apparatus according to this invention for desolvating flowing liquid streams while retaining temporal separation of dissolved solutes. LC techniques are generally well known in this art. As shown in FIG. 2, an isocratic or gradient Liquid Chromatography (LC) system 2500 is provided consisting of LC pump 2510, injector 2600 with associated sample loop 2605, sample loading syringe 2700 and waste bottle 2800. The LC system delivers the combined sample and solvent stream into chromatography column 2610. The LC eluent flows through capillary 2602 connected by compression fitting union 2607 to electrically heated thermal nebulizer 1700. The nebulizer 1700 is connected to cyclone 700 by compression fitting 2508. Sample travels from the cyclone 700 through the first-stage condenser tube 2900 to tee 3050 where condensed solvent drains into waste bottle 3100 and the aerosol travels through transfer line 3075, where pressure is monitored by gauge 3200, through second-stage condenser cold trap 3300 residing in liquid nitrogen cooled Dewar 3400. The aerosol then travels through transfer line 3450 and exits through nozzle 3500 where it deposits onto measurement surface 3600 inside vacuum chamber 3900. The vacuum chamber 3900 is evacuated by dual stage rotary oil roughing vacuum pump 4600. The thermal nebulizer 1700 is electric resistance heated. Electrical contacts 1710, connect adjustable nebulizer heating power supply 1300 and adjustable 4000 volt current limited bipolar DC solvent charging power supply 1600 to the nebulizer 1700 through connector 1400. A sheath of Teflon tubing (not shown) inside the union 2607 and compression fitting 2508 provides electrical isolation of the nebulizer 1700 from LC system 2500 and cyclone 700. Surface heaters 1900 in addition to surface heaters (not shown) on the bottom of cyclone 700 heat the cyclone to a controlled temperature. The cyclone temperatures are measured by thermocouples 1000, which provide signal to multi channel heater controller 1100, which powers heaters 1900. Tube 101 delivers nitrogen gas through heater 1910 regulated by thermocouple temperature sensor 1010 and powered by one channel of multi channel heater controller 1100. The temperature regulated nitrogen gas is delivered to either the top center inlet to the cyclone 700 or to alternate nitrogen inlet which connects through a compression fitting (not shown) to plenum 707 shown in FIG. 3B. Adjustable 4000 volt power supply 2100 can deliver current limited AC or DC high voltage to electrodes 900, or alternatively to electrode 1800, all of which are insulated by Teflon tubing as they enter the cyclone through compression fittings. The electrodes are insulated by a Teflon tubing sheath where they pass through the compression fittings. The electrodes 900 can produce a gas ionizing glow discharge inside the cyclone cavity. Adjustable 4000 volt bipolar DC power supply 2200 can provide a bias voltage offset to electrodes 900. Pressure gauge 800 monitors the cyclone toroid internal pressure while pressure gauge 1200 monitors the pressure in the cyclone outlet.

Figure 3A:
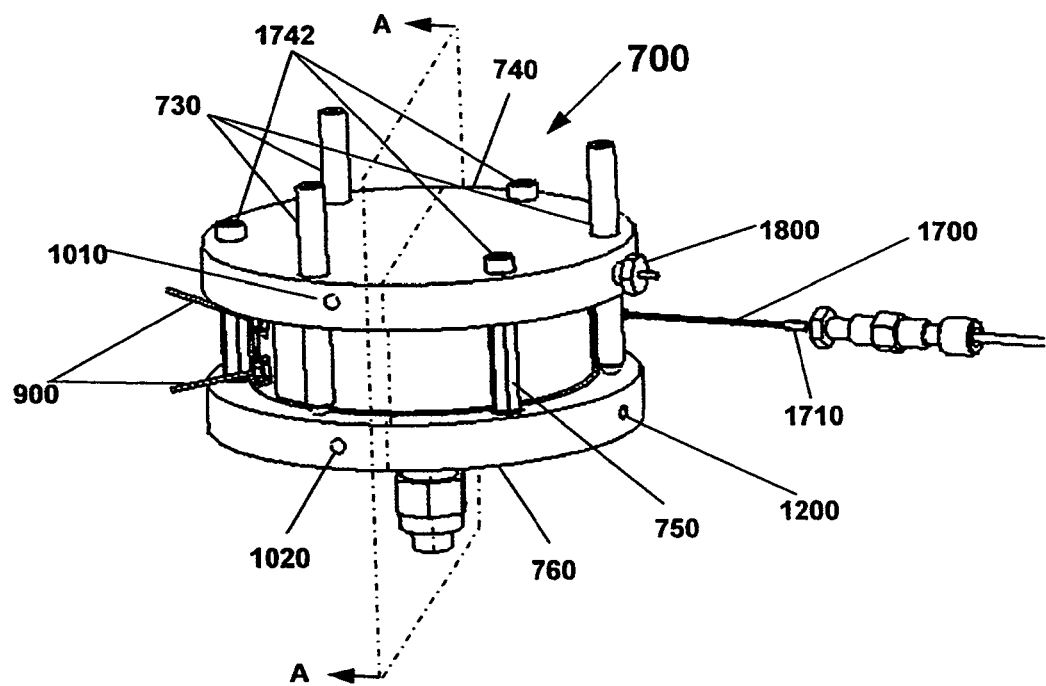
FIG. 3A is a schematic illustration of a first type of cyclone chamber according to an embodiment of the present invention
Figure 3B:
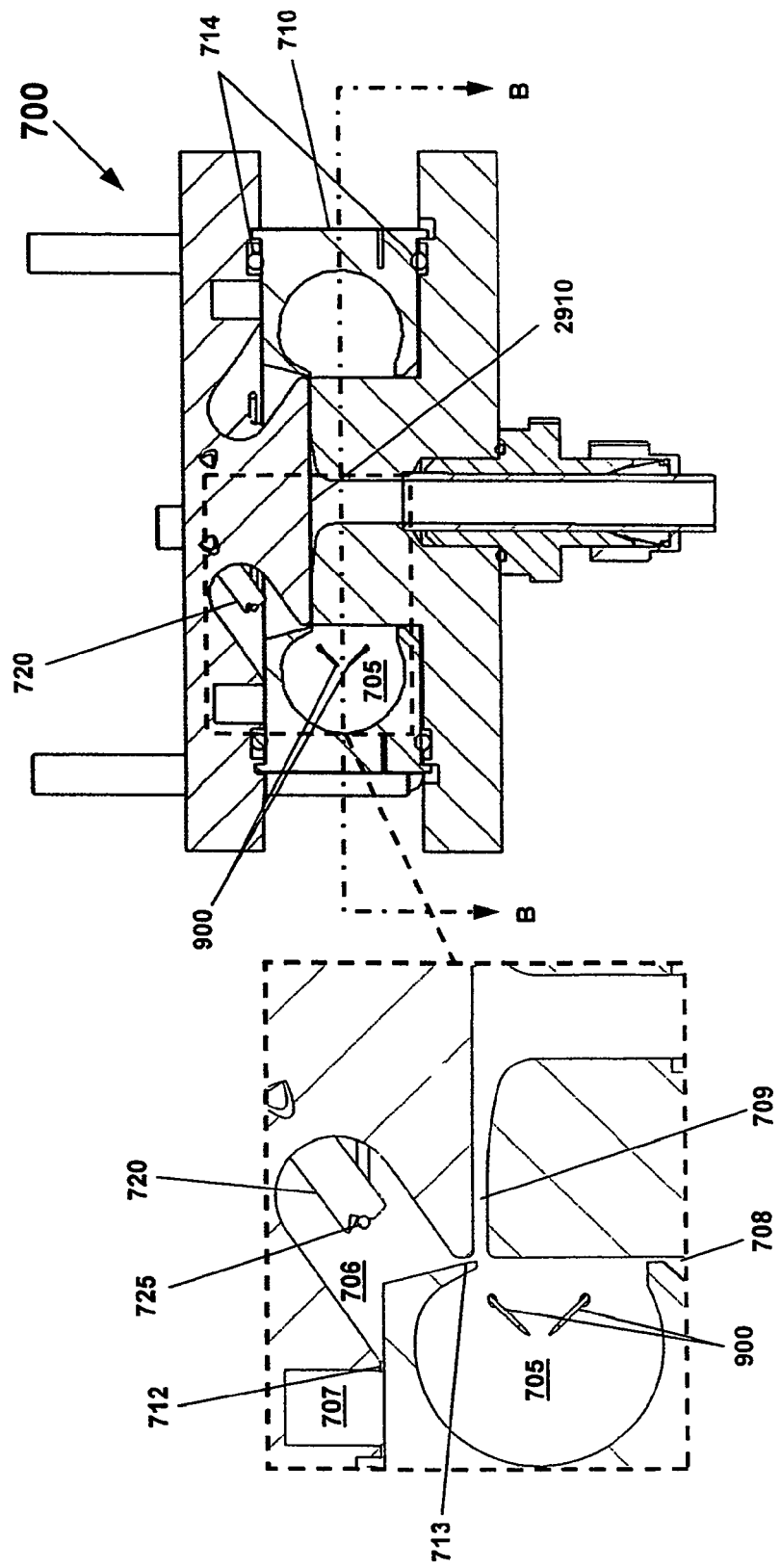
FIG. 3B is a section view of FIG. 3A along the vertical plane A-A through the central axis of the cyclone.
Figure 3C:
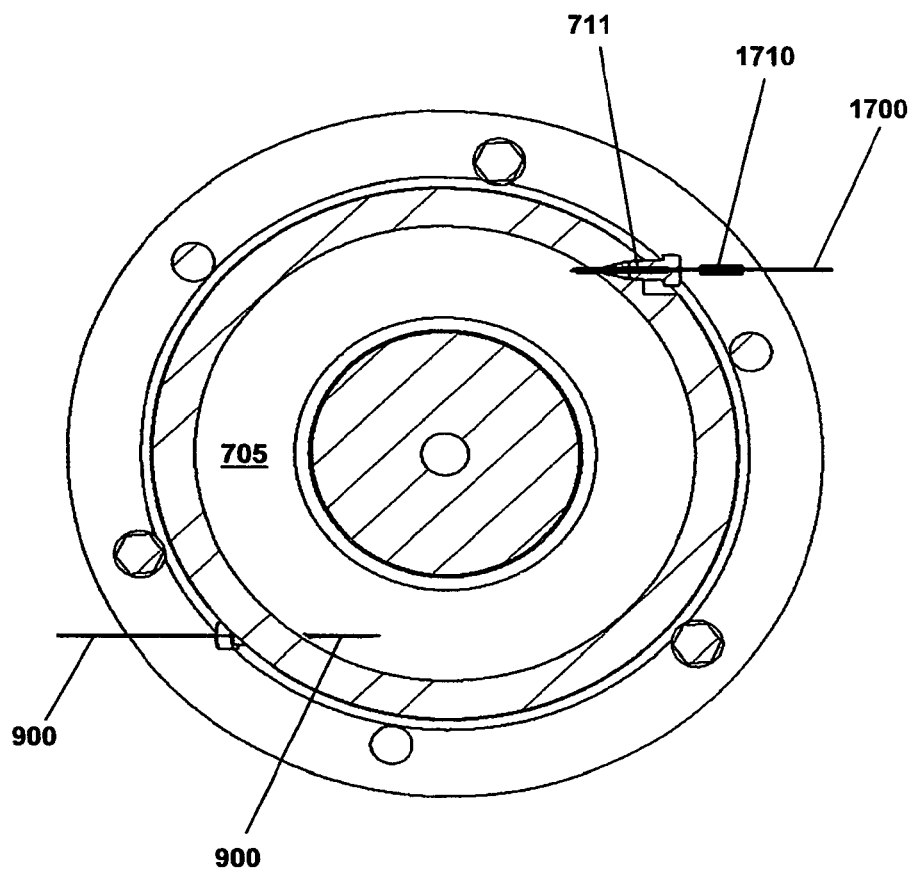
FIG. 3C is a top orthogonal view of the horizontal plane B-B through the largest cyclone cavity diameter as seen in FIG. 3B.

FIG. 3A shows a more detailed schematic illustration of a cyclone 700 such as is shown in FIG. 2, with the surface heaters omitted for clarity and an alternative central top gas entry port not shown. FIG. 3B is a vertical cross section schematic through the axis of the cyclone 700 along the plane A-A in FIG. 3A The inset showing an expanded region has the out-of-plane drawing lines removed to improve the clarity of illustration of the various gas passageways. FIG. 3C is a top view of the horizontal cross section through the center of the cyclone along plane B-B shown in FIG. 3B. These views show the cylindrical cavity 705 in the cyclone body 710 for droplet film boiling with the center of the top cover 740 and bottom cover 760 pushed inward to create a high shear gas exit path 709 to remove vorticity of the exiting solvent vapor and particles thereby creating an overall toroidal shape to the cyclone. The width of exit path 709 can be adjusted by jacking screws 730 and machine screws 1742 which hold the assembly together by screwing into hexagonal standoffs 750. O-rings 714 maintain a gas tight seal as the spacing exit path 709 width is adjusted. It was anticipated that the centripetal force associated with the dried droplet vorticity would extend into the condenser, causing many particles to be lost to the condenser walls. Experimentally, this feature appears to be unnecessary for the small cyclone sizes used to desolvate LC flows of under 2 ml/minute. Pressure tap 1200 connects to plenum 708, which connects to plenum 705 to monitor the pressure inside the toroidal cyclone. Cyclone bottom thermocouple port 1020, cyclone top thermocouple port 1010 and a thermocouple port (not shown) for the cyclone body 710 control the power to the heaters (not shown). The thermal nebulizer 1700 with its electrical contact 1710 enters through a Teflon tube inside compression fitting 711 at an angle that makes the outer edge of its spray cone roughly tangent to the outer diameter of the cyclone cavity 705. The inner diameter of the toroidal cavity 705 is chosen to be roughly tangent to the inner edge of the nebulizer spray cone, thereby avoiding escape of large droplets before they have been desolvated. Electrode pair 900 can be used to simultaneously create positive and negative ions in the cyclone evaporation chamber 705. Ring electrode 725 supported by insulating glass standoffs 720 connects to electrical feed through 1800 and can be used to create a glow discharge with only a single polarity of ions, or alternating single polarities. Gas enters (port not shown) plenum 707, which uniformly distributes the pressure around the diameter. Gas travels through the top to body gap 712 to enter glow discharge chamber 706 and then sweeps a small portions of the ions through gap 713 to join the desolvated droplets exiting through channel 709. Note that the alternative top center gas entry port used in FIG. 2 is not shown in this cyclone.

Figure 4A:
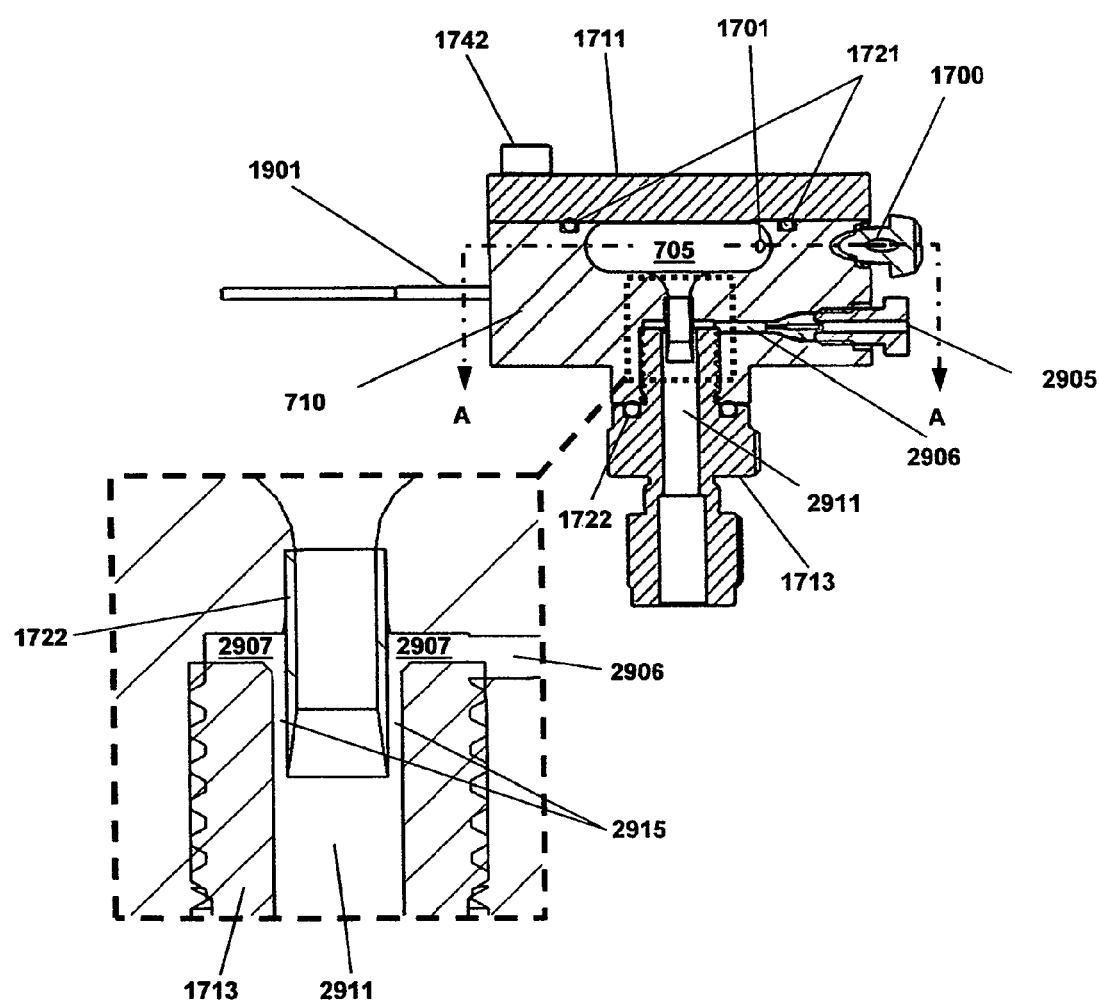
FIG. 4A is a schematic illustration of an alternative type of cyclone chamber (herein referred to as a sheathed flow gas addition cyclone chamber) according to an embodiment of the present invention.
Figure 4B:
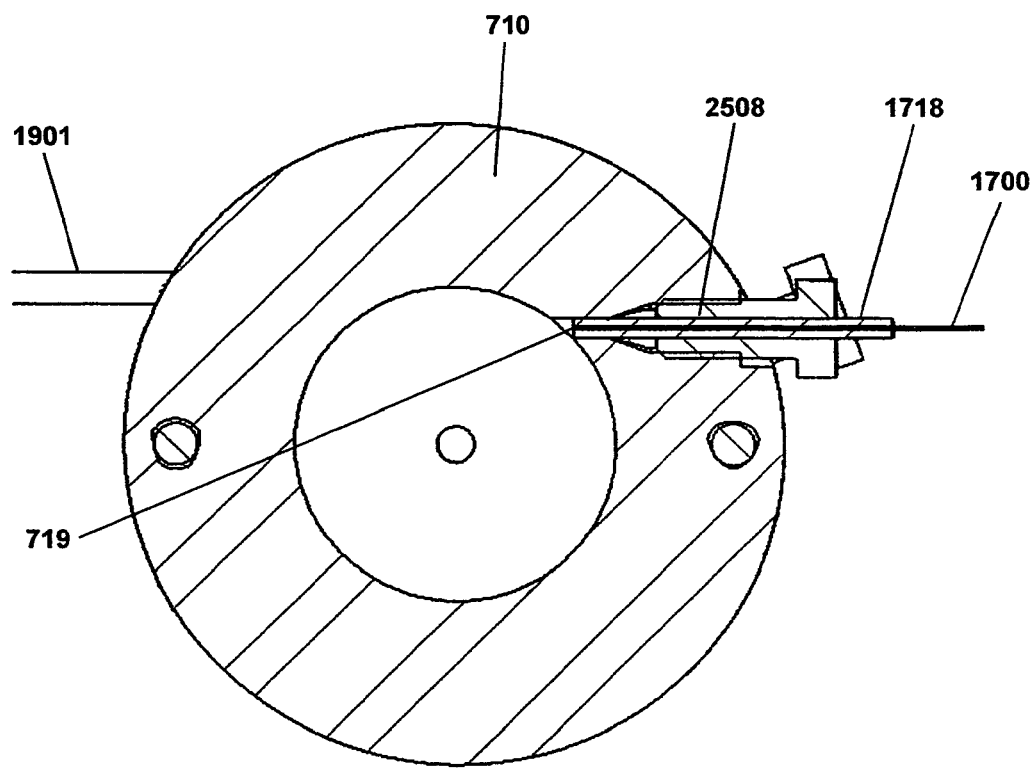
FIG. 4B is a top orthogonal view of the cyclone in FIG. 4A sectioned along the horizontal plane A-A bisecting the nebulizer unit 1700.

FIG. 4A and FIG. 4B are cross-sectional schematic illustrations of a preferred embodiment of the cyclone 700 in which the non-condensable gas creates a sheath surrounding the aerosol as it exits the cyclone. The inset showing an expanded region of FIG. 4A has the out of plane drawing lines removed to improve the clarity of the illustration of the various gas passageways. Cyclone body 710 has cyclone cover 1711 held on by machine screws 1742 (only one of 3 shown) and sealed by high temperature solvent resistant Kelraz O ring 1721. Thermal nebulizer 1700 is shown entering the cyclone body 710 through the machine screw of compression fitting 2508. The capillary nebulizer 1700 extends through the cyclone body 710. The tip 719 may extend slightly into the cyclone cavity 705, be flush with the cavity wall or be slightly recessed in the passageway 1701. For handling convenience, achieving a good electrical connection and compatibility with commercial 1.5 mm stainless steel compression fittings, the shown end of the nebulizer tube has been brazed into 1.5 mm outside diameter stainless steel tubing 1718. The aerosol exhaust from the cyclone travels through pressed-in tube 1721. The sheathing gas enters plenum 2907 through compression fitting 2905 and drilled passageway 2906. From plenum 2907 the gas travels through annulus 2915 to surround the aerosol as it enters condenser feed line inlet 2911, which in this embodiment is the central bore of compression fitting 1713. Compression fitting 1713 uses high temperature solvent resistant Kelrez O ring 1722 to seal to cyclone body 710. Cyclone body 710 is heated by cartridge heater 1901 and temperature is sensed by a thermocouple (not shown), both of which extend into the cyclone body.

Figure 5:
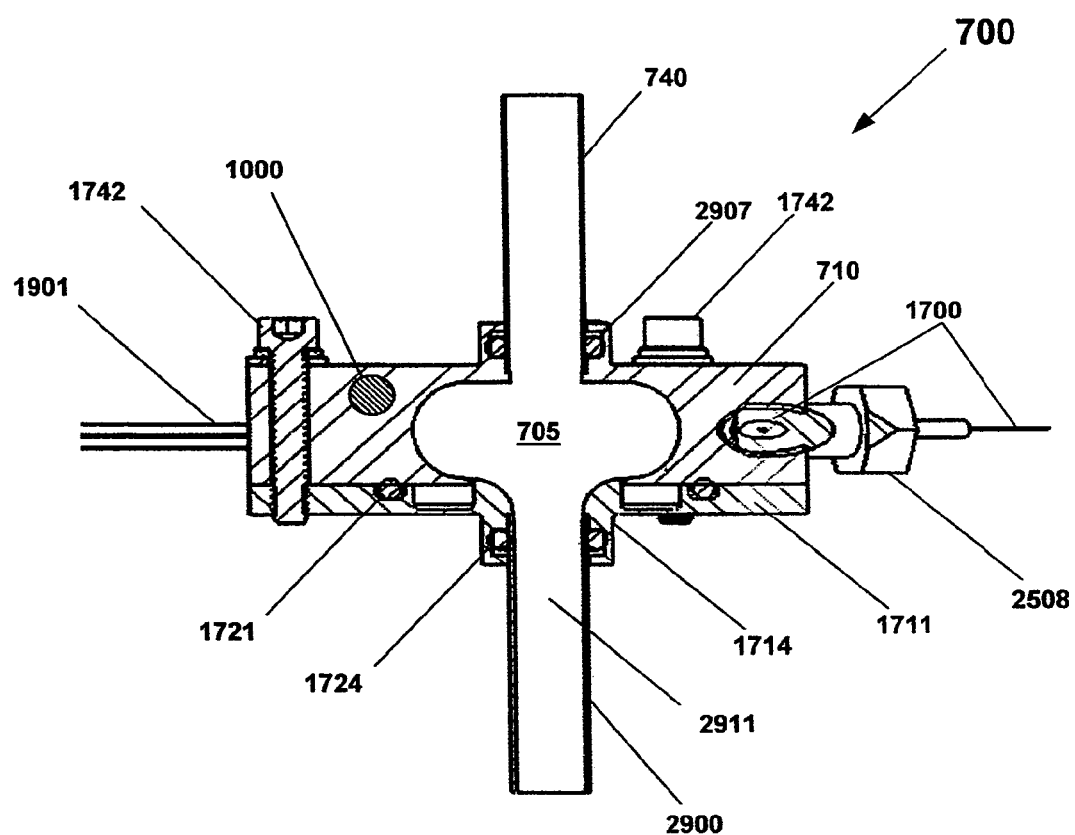
FIG. 5 is a schematic illustration of an alternative type of cyclone chamber (herein referred to as a cold quench gas addition cyclone chamber) according to another embodiment of the present invention.

FIG. 5 shows an alternative preferred embodiment schematic illustration of the cyclone 700 sectioned through the axis of the cyclone. The out-of-plane drawing lines have been removed to improve the clarity along the gas flow path. In this embodiment, the non-condensable gas enters the center of the cavity 705 through gas inlet tube 740 sealed to the cyclone body 710 by heat resistant O-ring 2907. Cyclone cover 1711 is sealed by O ring 1721 and held in place by machine screws 1742. The thin walled stainless steel first-stage condenser tube 2900 inlet end 2911 is sealed to the cyclone cover 1711 with O ring 1724 and is thermally isolated from some of the heat of the cyclone body 710 by thermal break thin section 1714. The cover 1711 on this cyclone was made of stainless steel for corrosion resistance and to minimize heat transfer to the first stage condenser tube 2900. Nebulizer 1700 is also shown with the spray directed out of the page. The cyclone cavity contents in FIG. 5 spins in the opposite direction from the cavity contents in the FIG. 4 illustration.

Figure 6:
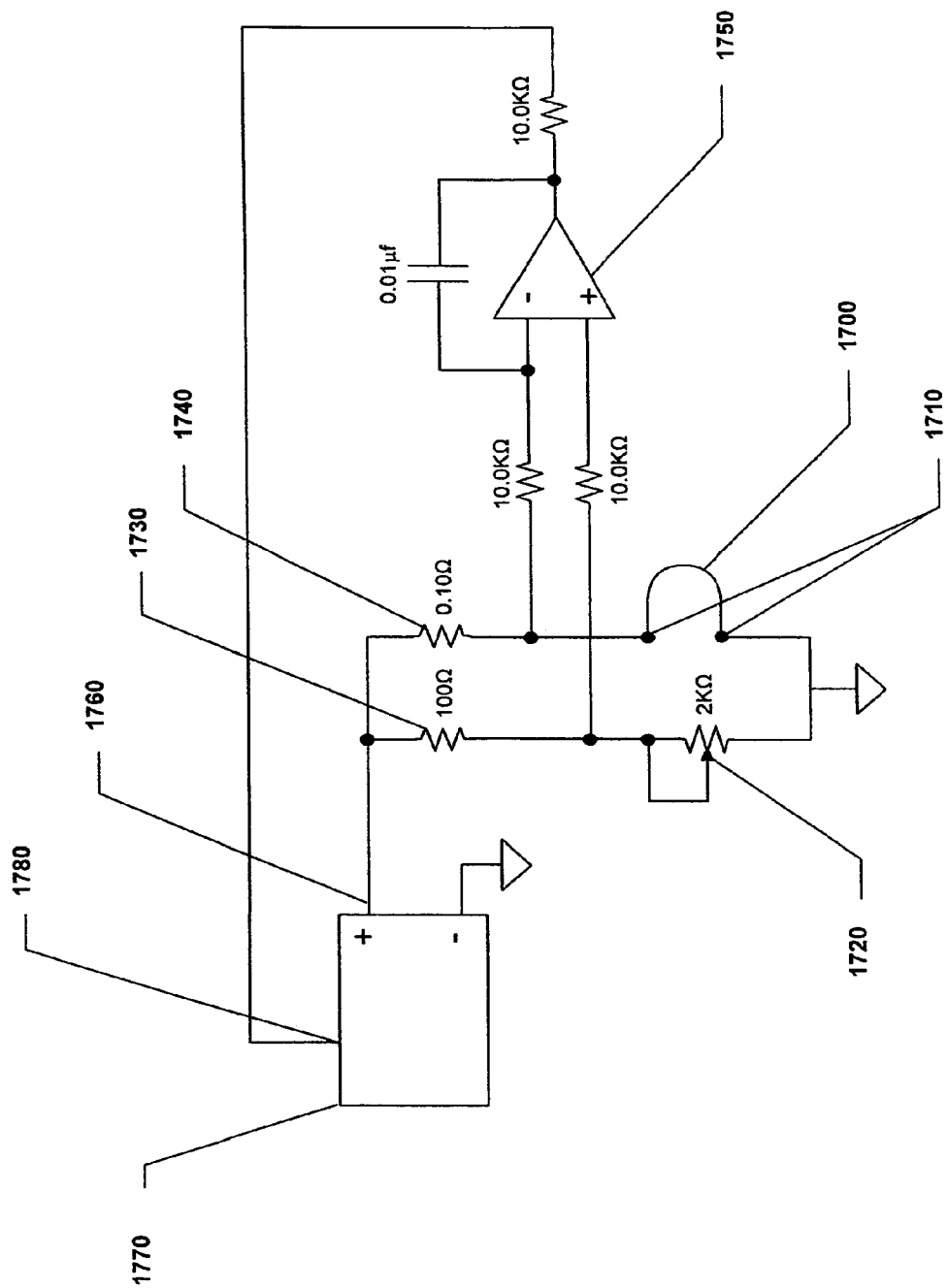
FIG. 6 is a schematic illustration of a thermal nebulizer control circuit according to an embodiment of the present invention.

FIG. 6 shows a preferred thermal nebulizer control circuit schematic. The capillary tube 1700 with electrical contacts 1710 forms one leg of a Wheatstone bridge made up of fixed resistors 1730 and 1740 as well as adjustable control resistor 1720. The output of the Wheatstone bridge as amplified by operational amplifier 1750 controls the set point 1780 of the adjustable DC power supply 1770. The DC supply output 1760 powers the Nebulizer through resistor 1740 and the reference voltage divider 1730 and 1720. Not shown is apparatus to measure the nebulizer power. The nebulizer power can be conveniently measured by multiplying the nebulizer current (as indicated by the voltage drop across resistor 1740) by the voltage across nebulizer 1700. A single integrated circuit (such as Analog Devices' AD633) can give a voltage proportional to the nebulizer power dissipation, which can be read by digital voltmeter. This power monitoring technology is well known to those skilled in the art.

Figure 7:
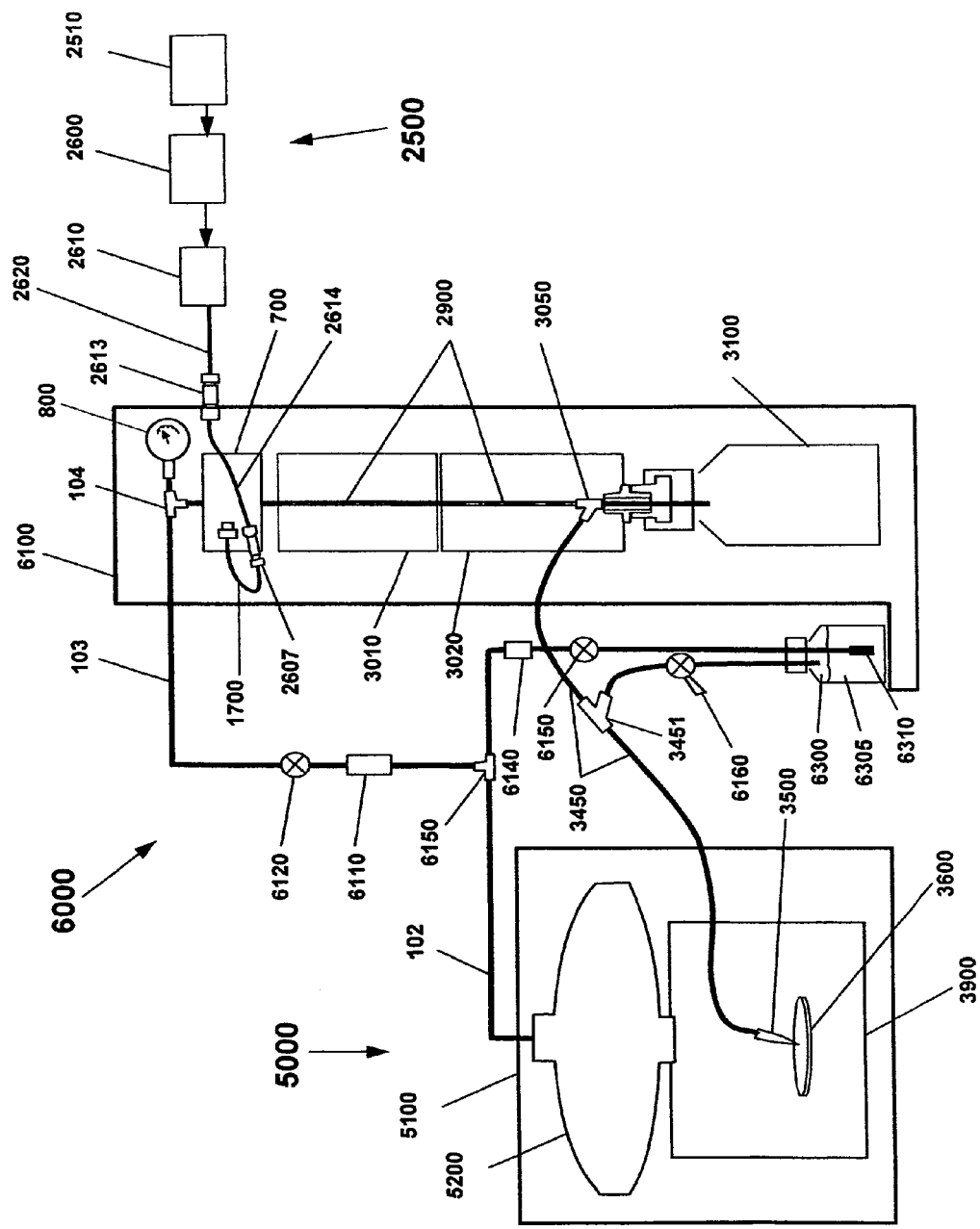
FIG. 7 is a schematic illustration of a single-stage condenser unit apparatus according to an embodiment of the present invention suitable for desolvating a Liquid Chromatograph (LC) stream followed by deposition of solute on an optical disk suitable for infrared detection.

FIG. 7 is a schematic illustration of the instant invention with a single stage condenser, a product which has recently become commercially available from the assignee of this invention Spectra Analysis, Inc. Marlborough, MA 01752, USA, under the tradename DISCOVIR-LC™. The operation of this product is described in the "DiscovIR Operating Manual, Infra-Red Detector for GC and LC", Part Number DC00001, dated Sep. 2007, which is included herein by reference. The commercial product consists of a computer-based data and control system, a Direct Deposition Fourier Transform Infrared spectrometer module, and an LC interface module. Also shown in FIG. 7 is LC system 2500 consisting of LC pump 2510, which delivers solvent to injector 2600, which delivers solvent and sample to chromatographic column 2610. The LC eluent stream passes through capillary tube 2620 to bulkhead union 2613 mounted on LC interface module chassis 6100. Fused silica capillary 2614 delivers the eluent stream to the thermal nebulizer 1700 while electrically isolating it from the bulkhead union 2613, which is at the same ground electrical potential as LC interface module chassis 6100. The thermal nebulizer is electrically connected through union 2607 and the cyclone assembly 700 to the nebulizer control and power supply (not shown). The evaporated aerosol stream from the cyclone 700 travels through the first-stage condenser thin walled stainless steel tube 2900 that is cooled initially by forced air over fins 3010 and then by a temperature regulated Peltier heat pump 3020 the hot side of which is also forced air cooled. "Y" connection 3050 separates the condensed solvent, which drains into waste bottle 3100, from the sample containing aerosol, which travels through Teflon tube 3450 into Direct Deposition Fourier Transform Infrared spectrometer module chassis 5100 and into vacuum chamber 3900 where transition into vacuum through nozzle 3500 focuses the aerosol particles for deposition onto an infrared transparent optical disk 3600. The disk 3600 is cooled by liquid nitrogen Dewar 5200 and thermally regulated by heaters, temperature sensors and controls that are not shown. The disk 3600 rotates and translates under computer control so the solids from a chromatogram are sequentially deposited along a spiral track. The disk motion carries the deposited spiral track through the 0.1 mm focused beam of a Fourier transform infrared (FTIR) transmission spectrometer. Nitrogen gas, released by liquid nitrogen Dewar 5200 is collected, warmed to approximately ambient temperature and delivered through tube 102 to tee 6150, then through flow sensor 6110, flow regulating needle valve 6120, tube 103 and tee 104 to the cyclone 700. Tee connection 104 also connects to pressure gauge 800, which monitors the cyclone pressure. Excess nitrogen gas is used to purge the optical path of the FTIR in the Direct Deposition Fourier Transform Infrared spectrometer module (not shown). Bottle 6300 contains an adhesion promoter 6305. When used, this typically liquid adhesion promoter is delivered to the disk 3600 by taking nitrogen gas from tee 6150, passing the gas through flow sensor 6140, regulating the flow with needle valve 6150 and passing the gas flow through fine frit 6310 located beneath, or submerged in the adhesion promoter 6305. The nitrogen gas collects adhesion promoter vapor and carries it through shut off valve 6160 and at "Y" connection 3451 enters transfer line 3450 where it is carried with the sample to the disk 3600. The adhesion promoter bottle and flow path to "Y" 3451 may be temperature controlled to change the ratio of adhesion promoter to carrier gas, and prevent condensation prior to dilution with the aerosol analyte plus non-condensable gas stream. The function of the adhesion promoter is to form a small puddle of condensate on sample disk 3600 at the focus of the nozzle 3500. This puddle prevents aerosol particles from bouncing when they strike disk 3600 by dissipating the kinetic energy associated with the aerosol particle impact. The "bounce" problem appears to be limited to materials that form very elastic particles, such as polystyrene. Empirically these appear to be materials that are below their glass transition temperature. By using an adhesion promoter with a lower vapor pressure than the solvent, yet high enough to completely sublime off the disk before traveling into the FTIR beam (typically 20 seconds to several minutes) a small controlled puddle size can be obtained by precisely controlling the amount of adhesion promoter delivered to the disk. In addition to vapor pressure, miscibility with the solvent systems or more precisely capable of dissolving the sample is desirable. 2-methoxyethanol is an example of a good adhesion promoter. Condensation of residual solvent on the disk can perform the same function as the adhesion promoter, but it is difficult to control the disk temperature accurately enough to maintain the solvent puddle at a stable small size.

FIG. 8 shows a two-stage condenser version of the instant invention. The LC, and Direct Deposition Fourier Transform Infrared spectrometer modules, have all their components and identification numbers the same as in FIG. 7. The cyclone and first-stage condenser are also in common with FIG. 7. The differences are in treatment of the nitrogen gas source and second-stage condenser. With the second-stage condenser system, cold nitrogen gas from the Dewar 5200 is removed without heating by dip tube 3340, which extends from inside the Dewar through insulated Dewar cap 3345 and is sealed to insulated Teflon tube 3350. The cold nitrogen gas travels through controlled tempering heater 3300 located internal to insulated tube 3350 which then coaxially surrounds and cools the second-stage condenser tube 3445 forming a counter flow heat exchanger. Thermocouple 3320, located on the outer wall of the inner tube 3445 of the second-stage condenser 2950 through a temperature controller (not shown) regulates the heat applied to heater 3300, thereby regulating the temperature of the second-stage condenser. After cooling the second-stage condenser, the nitrogen is directed through an internal passage 3360 in the metal block, which thermally connects the Peltier heat pump 3020 cold side to the first-stage condenser tube 2900. This warms the nitrogen gas while providing additional cooling capacity to augment the Peltier heat pump. The partially warmed nitrogen gas then travels through tubing coil 2955 which is located in the warm air forced exhaust stream from the air cooled portion of the first-stage condenser 3010. The nitrogen gas, warmed to approximately room temperature, travels through tee 6250, which supplies the nitrogen demands of the LC interface module with the excess nitrogen 6350 going to purge water vapor and $CO_2$ out of the optical path of the Direct Deposition Fourier Transform Infrared spectrometer module. Tube 6340 supplies nitrogen to tee 6150 with carrier gas for the cyclone 700 by way of flow sensor 6110 and flow regulating needle valve 6120. Nitrogen for the second-stage condenser freezing point depressant delivery system flows through flow sensor 6140, flow regulating needle valve 6150, frit 6410 located in bottle 6300 submerged under the freezing point depressing solvent 6405, and after entraining the freeze point depressing solvent vapor travels through shut off valve 6160 and into injection needle 6170 which carries the nitrogen vapor mix into the inlet to the second-stage condenser. The freezing point depressant delivery system may be controlled at elevated temperature to increase the ratio of freezing point depressant to nitrogen. Desirable freezing point depressants are miscible in all ratios with the solvents being used, have a very low freezing point, and have a very low vapor pressure at their freezing point. Methanol is an example of an excellent freezing point depressant, especially for aqueous solvent systems.

FIG. 9A is a schematic illustration of the LC interface module hardware shown in FIG. 8. FIG. 9B is an orthogonal section view from the right side of FIG. 9A. FIGS. 9A and FIG. 9B use the same designator numbers as FIG. 8. For clarity only a few of the heat exchanger fins are shown. Adjustable control resistor 1720 is used to set the nebulizer power at known solvent delivery conditions. FIG. 10 is a schematic illustration of an alternative multi-stage condenser system. Not shown is the thermal insulation. Cold thermally regulated nitrogen gas is delivered through insulated tube 3350 to the insulated third stage counter flow heat exchanger 2955 and then to insulated second-stage heat exchanger 2950 and then travels the same path as in FIG. 8 and FIG. 9. After being separated from first-stage condensate at the down hill "Y" connection 3051, the aerosol sample travels through the inside of the second-stage condenser tube 2980, is separated from condensate at "T" block 3052 with condensate collected in second and third stage waste bottle 3101, and the aerosol continuing through tube 3450 which constitutes first the inside of the third-stage condenser and after traveling through reducing "T" connection 3053 becomes the sample transfer line.

FIG. 11A is a chromatogram displaying the maximum absorbance at any wave number from about 650 inverse centimeters to 4000 inverse centimeters. The chromatogram was collected using the apparatus shown in FIG. 7 with the nebulizer control circuit shown in FIG. 6. The chromatography used a 10 minute reverse phase gradient at 1 ml/minute from 98% water/2% methanol to 100% methanol on a C18 Nova-Pak column. The cyclone temperature was 180 degrees Celsius and the nebulizer power was set to 14 watts at initial conditions. The X axis is time in minutes and the Y axis is absorbance in absorbance units. FIG. 11B is the FTIR single scan spectrum of theobromine, taken at the apex of the 5.87 minute peak in FIG. 11A. The X axis is wave number in inverse centimeters ($cm^{-1}$) and the Y axis is the absorbance in absorbance units.

FIG. 12 is a flow injection spectrum of Gamma Hydroxy Butyric Acid (GHB) produced using the apparatus shown in FIG. 8. The sodium salt of GHB is thermally unstable and readily cyclizes to the lactone in a gas chromatograph. The spectra clearly shows the uncyclized form Note the Carboxylic group at 1561 and the OH group at 3319. The X axis is wave number in inverse centimeters ($cm^{-1}$) and the Y axis is transmittance in %.

Figure 1:
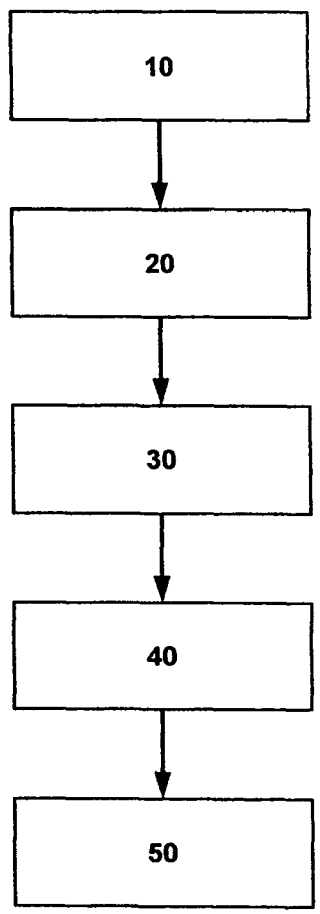
FIG. 1 is a process flow diagram illustrating the major steps of one embodiment of the invention.

Referring now to FIG. 1, typical process steps in the method of this invention include the following:

Liquid Stream Generation Step (10):

In step (10), a flowing liquid sample stream containing dissolved and/or dispersed materials in various sections of the stream is generated. The liquid sample stream to be treated in accordance with this invention might originate, for example, as the eluate from a liquid chromatograph column 2610, or from a flow injection apparatus (pump 2510 and injector 2600), or as a stream of relatively steady composition from a pump or a pressurized source such as a manufacturing process.

Nebulization Step (20):

In step (20) the flowing liquid sample stream, or a portion thereof, is nebulized, which converts the liquid stream into a gas and/or solvent vapor plus sample containing solvent droplet aerosol stream. A flow of a substantially inert non-condensable gas (such as air, nitrogen or helium), or a condensable gas (such as water or other solvent vapor) may be added to assist in the nebulization process. Various types of known nebulizer devices may be used in this step, including pneumatic nebulizers of either concentric flow or cross flow geometry, electrospray nebulizers, sonic and ultrasonic nebulizers, spinning rotary disk nebulizers, thermal nebulizers or combination nebulizers. The nebulizer selected needs to be of suitable size relative to the flow rate of the liquid stream to be treated. A particularly preferred embodiment for purposes of this invention is a thermal nebulizer without a gas addition, or a combined thermal and concentric pneumatic nebulizer using a volume of non-condensable gas substantially less that the resultant solvent vapor volume. If large volumes of gas are needed for nebulization, a condensable gas such as water or solvent vapor can be used. In one preferred embodiment, the thermal nebulizer is a short heated capillary tube 1700 (as seen in FIG. 2), preferably between 1 and 20 cm in length with an inside diameter between 0.05 and 0.2 mm The eluent stream temperature rises substantially above its discharge pressure boiling point as it passes through the capillary nebulizer. As demonstrated by the prior thermospray art, the very short duration of sample exposure to high temperature prevents its degradation. The prior art has shown that as the fluid flows through the capillary, the pressure drops and the superheated liquid partially evaporates to the gas phase. The high shear force of the expanding volume of gas produces a very fine relatively uniform nebulization. To ensure good thermal nebulization, the nebulizer apparatus of this invention should heat the fluid stream to a superheated temperature that is more than 20° C., preferably at least 50° C., and more preferably at least 100° C., above the boiling point of the liquid component of the fluid stream being treated at the capillary discharge end pressure. In the present invention, it is preferable to operate the thermal nebulizer between 10% and 99% evaporation, and more preferably between 40% and 80% evaporation. Some heat transfers to the nebulizer from the cyclone body 710. It is preferable to make this heat transfer small so that a wide range of nebulizer evaporation control can be exerted independent of the cyclone temperature.

In the present invention, a preferred way to provide heat input to a thermal nebulizer is to make it of a corrosion resistant conductive metal capillary tube such as stainless steel or nickel and passing electrical current from power supply 1300 (as shown in FIG. 2) along the length of the capillary tube. Operating with partial solvent evaporation improves the nebulizer stability.

If the thermal nebulizer is used without a thermal feedback control system, the maximum desirable power input is determined so any drop in flow rate and reduction in sensible and latent heat capacity due to solvent composition change will not cause 100% evaporation, as the solids will then precipitate out of solution and may plug the nebulizer. Even if plugging does not occur, when all the solvent evaporates the nebulizer temperature increases and the solute may be damaged by exposure to the high resulting temperature. In the extreme case where liquid flow stops and the power is not reduced, the metal capillary may melt. The minimum desirable power is determined to maintain good nebulization when any flow rate increase or increase in sensible and latent heat capacity occurs. In the prior art a thermal nebulizer used with gradient LC requires changes in control settings as the gradient progresses.

The prior art typically controlled either the power input or the temperature of a relatively large block of metal that the capillary passed through. It is speculated that this resulted in a significant thermal lag and a large temperature gradient between the temperature controlled location and the inner capillary surface. The temperature gradient resulted in a substantially different temperature at the control point and the capillary inner surface that transfers heat to the eluent stream. Therefore the temperature set point was typically substantially higher than the actual capillary inner surface temperature, which was not determinable. Empirically, any eluent change (composition or flow) required a change in control set point. Therefore sophisticated thermal nebulizers used with LC gradients would incorporate preprogrammed changes in set points that were correlated to the gradient conditions.

According to the present invention, automatic stable nebulizer performance over large changes in both solvent composition and flow rate can be obtained by a control system that substantially maintains the total electrical resistance of the capillary nebulizer near to a predetermined value. To assist in understanding, a theory of why this works will be presented, although validity of the invention should not be predicated on correctness of this theory. Because the electrical resistance of the capillary tube varies approximately linearly with temperature over the control range, maintaining a constant total capillary electrical resistance is believed to be tantamount to maintaining a stable average capillary temperature. The temperature distribution along the capillary length may vary, but the (resistance weighted) temperature average along the length of the capillary is maintained substantially constant. The low heat capacity of the capillary allows the control loop to respond rapidly to changing solvent conditions. The heat capacity of the capillary should be substantially less than the heat capacity of the fluid contained in the capillary. For example, the heat capacity of the capillary might advantageously be less than $\frac{1}{10}^{th}$ that of the fluid in the capillary, preferably less than $\frac{1}{100}^{th}$, more preferably less than $\frac{1}{1,000}^{th}$. The thin wall of the capillary results in a relatively small temperature difference the bulk of the capillary where the heat is generated and the inner capillary surface where the heat is transferred to the solvent stream. In the present invention, which desirably uses a capillary having a wall thickness of a fraction of a millimeter, more desirably having a wall thickness between about 0.1 mm and 0.02 mm, or in the example given having a wall thickness of 0.05 mm, it is believed that each location along the length of the capillary, has a relatively small temperature difference between average across the wall and the inner surface. In the present invention it is found that a single control setting results in stable nebulizer operation over the varying solvent composition and flow conditions that occur during typical gradient LC separations. A reversed phase separation from 100% water to 100% organic solvent such as methanol or acetonitrile (including perturbations resulting from pump pulsations, solvent viscosity variations, etc. as well as programmed flow changes) can be dramatically improved by automatically varying the voltage (and resulting current) to the nebulizer in a manner that maintains the nebulizer electrical resistance nearly constant. Convenient electrical contact to the capillary can either be through dedicated electrical high temperature soldered or crimp on connectors 1710 or through conductive compression fittings that support and hydraulically connect the capillary. When using the compression fittings for electrical contact, electrical isolation of the nebulizer can be provided by electrically floating either the LC system or the cyclone, or making a section of the interconnecting capillary tube 2600 of insulating material well know to those skilled in the art, such as PEEK or fused silica. The low thermal inertia of the capillary tube makes the energy input to the stream nearly instantaneously determined by the electrical power applied to the capillary. This allows a feed back control to maintain the % evaporation within acceptable limits, even under conditions of rapidly changing flow and solvent composition. Adjustable control resistor 1720 sets the desired electrical resistance (temperature) of the nebulizer tube. If the nebulizer tube cools the nebulizer resistance becomes lower causing the operational amplifier 1750 output to call for more voltage from the DC power supply. This higher voltage increases the current through the nebulizer until the nebulizer has heated up sufficiently to increase its resistance sufficiently to balance the bridge and reduce the call for more voltage.

In the instant example, it is found that a single setting of the control circuit automatically adjusts the nebulizer power to accommodate wide changes in solvent composition (from pure water to pure organic solvent) and flow rate (from 0.2 to 2 ml per minute). The DC power supply output 1760 automatically adjusts from about 0 to 15 volts and can deliver up to 40 watts to the nebulizer. This allows operation up to 2 ml per minute of any solvent. A desirable way to set the nebulizer operating condition (electrical resistance) is to flow a known solvent at a known flow rate through the nebulizer. The control resistor 1720 is then adjusted until the power dissipated in nebulizer 1700 is the desired % of the theoretical sensible plus latent heat required for total evaporation. At one milliliter per minute, the approximate theoretical power required to fully evaporate some typical LC solvents are: chloroform 8 watts, acetonitrile 9 watts, tetrahydrafuran 10 watts, isooctane 11 watts, isopropyl alcohol 15 watts, methanol 22 watts, trichlorobenzene 25 watts, DMSO 35 watts and water 44 watts. It is experimentally found that a good power to adjust to is about 4 watts less than the theoretical 50% evaporation requirement. It is speculated that this empirical 4 watt offset is because of heat transferred to the nebulizer 1700 by thermal conduction from the cyclone body. In the instant example, solvents like chloroform and pure acetonitrile can be successfully nebulized with no applied electrical power. When operating LC gradients, the nebulizer power is best set using that gradient's highest power requirement composition and flow conditions. For a water to acetonitrile gradient at 1 ml per minute, the power should be set to about 18 watts while flowing at initial conditions of 1 ml per minute of 100% water. The desired power calculation for this example is: 50% of 44 watts for 100% evaporation of water at 1 ml per minute which is 22 watts, less 4 watts gives 18 watts for the set point Empirically it is found that good results can be obtained over a fairly wide range of set points. It is also empirically found that after setting the nebulizer power, the automatic control protects the nebulizer from damage even if the flow totally stops.

Desolvation/Evaporation Step (30):

In step (30), the next process step, evaporation in the cyclone converts the aerosol in the nebulized stream to vapor plus highly concentrated, typically dry particles of the low-volatility component(s). The high-speed aerosol jet from the nebulizer 1700 is directed circumferentially around the hot, generally cylindrical shaped outer diameter of the cavity 705 inside of the cyclone. In one embodiment, the cyclone was designed with the cylindrical cavity having a reduced width exhaust passageway from cavity 705 to the central gas exit, which results in an overall toroidal-like cavity. The central core of the toroid shown in FIG. 3 may optionally be removed to make an open cylinder as shown in FIGS. 4 and 5 cross section views. Centrifugal force from the jet velocity causes the larger liquid droplets to travel along the outer diameter of the cavity. The cavity surface is heated to cause the droplets to film boil. The polyimide or silicone-covered thin metal film heater 1900 and/or electric cartridge heater 1901 is/are powered from a temperature controller (not shown) with temperatures being sensed by thermocouple(s) 1000. Cyclone heat can be supplied by many different types of heating sources including the following: an electric resistance heater; an electric cartridge heater, a surface-mounted electric resistance heater; a deposited film electrically-conductive resistance heater; an electrically-conductive heater deposited along at least a portion of the cylindrical-shaped chamber cavity surface; a radio frequency electrical induction heater, a microwave heater; a flame; an infrared radiant heater; a high-temperature gas; steam; and high-temperature liquids such as molten salt or superheated water. While not essential, it is desirable to fabricate the cyclone of highly thermally conductive material to minimize the temperature differences between the inner surface of the cyclone and the temperature sensing and heat delivery locations. At operating temperature, the inner surface of the cyclone should resist corrosion from the solvents and samples. The cyclone examples presented herein were made of nickel-plated aluminum. Film boiling rapidly evaporates solvent from the droplets. In film boiling, the freshly evaporated solvent vapor exiting a droplet acts as a gas cushion that prevents the droplet coming in contact with the cavity wall. The solute is thereby retained in the droplets. The solute structural integrity is preserved because the maximum solute temperature is limited by setting the "boiling point" through regulation of the cyclone chamber pressure into which the solvent evaporates from the droplets. This may desirably be operated below atmospheric pressure. When the droplets are sufficiently small, Stokes drag from the exiting solvent vapor carries the droplets out along the central axis of the cylindrical cavity. After exiting the surface vicinity, the superheated solvent vapor further dries the droplets. Since the additional drying takes place by transferring the residual super heat in the solvent vapor to all entrained droplets (partially equilibrating the temperatures) the degree of super heat of the solvent vapor (affected by solvent flow rate, cylinder temperature and dimensions), cylinder dimensions (which affects residence time), length of travel before cooling and number (total mass) of exiting droplets relative to exiting solvent vapor mass help determine the amount of additional drying that takes place after droplets leave the region of the cylinder surface. For the chromatographic application with solvent flows between 0.2 and 2 ml 1 minute, the cylinder is preferably maintained between 100 and 400 centigrade, 10 and 0.3 centimeters in diameter and 10 and 0.3 centimeters long. More preferably the cylinder is maintained between 150 and 250 centigrade, 5 and 1 centimeter diameter and 2 and 1 centimeters long. It is desirable to avoid sharp corners and irregularities that would interfere with suspended droplet motion or smooth fluid flow. If not already present, a quantity of non-condensable gas, such as nitrogen from tube 101, 2906, or 740 is added. The amount, location, degree of mixing and temperature of the added gas also influences the amount of additional drying which takes place after a droplet leaves the cyclone surface. Excessive drying should be avoided as this can result in loss of volatile samples.

One desirable place to add the non-condensable gas is as a sheathing flow 2915 around the inside diameter of the condenser feed line inlet 2911. This maximizes the particle suspension in the condenser while minimizing the total amount of non-condensable gas required for particle suspension. Alternative preferred cylindrical cyclone evaporators are shown in FIG. 4 and FIG. 5. FIG. 4 shows gas addition as a sheathed flow 2915 immediately after the cyclone. FIG. 5 shows a cool gas addition into the top center of the cyclone to rapidly cool the aerosol and reduce the amount of drying that takes place after droplets leave the cyclone surface. The hot cyclone chamber 705 is thermally isolated from the gas inlet tube 740, which is low thermal conductivity thin walled stainless steel tubing. The cyclone 700 to condenser tube, typically the top portion of first-stage condenser tube 2900, is also thin walled stainless steel to minimize axial thermal conduction. If the mass of gas addition is made comparable to the mass flow of the superheated solvent vapor, further evaporation and loss of volatile samples can be reduced. This is particularly dramatic for low concentrations of volatile samples. The trade off between complete solvent evaporation and minimizing solute loss can be partially regulated by controlling the temperature and mass of the gas addition. In FIG. 2, the gas addition temperature can be raised by heater 1910, sensed by temperature sensor 1010 and controlled by the thermal controller (not shown). This gas preheat feature was not incorporated into the apparatus shown in FIG. 7 and FIG. 8.

Electrostatic charge can dramatically effect the droplet size distribution both during the nebulization process and during the droplet shrinking process as the solvent is evaporated, as discussed for example in "Aerosol Technology: Properties, Behavior, and Measurement of Airborne Particles" by William C. Hinds (second edition 1999, John Wiley & Sons, Inc.) which is incorporated herein by reference. The number of droplets can be partially controlled by controlling the electrostatic charge present on droplets. When charged droplets evaporate, they shrink until the electrostatic repulsion forces become great enough to cause a coulomb explosion creating a large number of smaller droplets. Since the disclosed cylindrical film boiling cyclone ejects partially desolvated droplets at a relatively fixed size independent of the number of droplets present, the ratio of droplet mss to super heated solvent vapor is affected by the number of droplets. Electrospray nebulizers produce small charged droplets by electrostatic repulsion of the liquid from the needle. High speed liquid streams (thermospray) strip the electrostatic double layer out of their delivery tube (called streaming current) and can result in charged droplets. Increasing the electrostatic charge on the nozzle can increase the degree of droplet charging during nebulization, which through coulombic explosion produces more droplets each containing less solute. The electrostatic charge on the droplets can also cause droplet and dried droplet loss to the walls. Adjustable 4000 volt bipolar DC solvent charging power supply 1600 controls the potential of, or current to the thermospray inlet to the cyclone. In FIG. 3, the conductive capillary 1700 is electrically insulated from the cyclone body by a thin Teflon sheath. This power supply can also be used to counteract the streaming charge thus increasing the initial droplet size and reducing the total number of droplets formed. Droplet charging and dried droplet charge can also be increased or reduced by exposure to high mobility ions produced by a glow discharge. A bipolar glow discharge can be used to reduce the total amount of charge present (as discussed in the Hinds publication at pages 316-347.) This can be delivered to electrodes 900 by adjustable 4000 volt bipolar AC/DC current-limited power supply 2100. This discharge can be biased to produce more positive or negative ions by adjustable current limited bipolar high voltage DC power supply 2200. Droplet charging of either polarity can be created by a unipolar glow discharge or affected by an alternating positive and negative discharge coming from the single wire ring electrode 725 supported by glass electrode standoffs 720. Use of these electrostatic controls are an optional part of the disclosed invention, and are not necessary for many operating conditions in the chromatography application.

Another way to affect electrostatic charge is by the addition of volatile buffers that readily produce gas phase ions. These ions are capable of transferring charge from droplets. Ammonium acetate is an example.

Concentration Step (40):

In step (40), the bulk of the condensable gas is removed from the desolvated flowing stream while retaining a significant portion of the dried particles entrained in that stream. Solvent vapor is removed by condensation onto the inside of a condenser tube 2900 cooled by ice water bath 3000 (FIG. 2) or air cooled condenser 3010 followed by Peltier electronic cooler 3020, as seen in FIG. 7, FIG. 8 and FIG. 9. An air-cooled section of the first-stage condenser is used to reduce the heat load on the Peltier cooled section of the first-stage condenser. The vast majority of the latent heat released during condensation of solvents like water occurs in the air-cooled section. Stokes drag from the non-condensable gas maintains a significant portion of the dried droplets in suspension away from the condenser walls. The condensed liquid solvent is collected in waste bottle 3100 after being separated from the dried droplet carrying gas stream by gravity at "Y" 3050. Collecting the condensed solvent as a liquid and removing it from the dried aerosol flow path is desirable in chromatographic applications, as it minimizes the volume otherwise needed to store the condensed solvent. In the preferred embodiment where the liquid is drained, the temperature of the condenser tube 2900 is above the freezing point of the liquid condensate, and the liquid path is continuously descending to the separation tee and the gas path is then continuously ascending until it is beyond the last cold location where liquid is expected to condense. Excess flow path volume is undesirable as it causes bandspreading of chromatographic peaks. For the chromatographic application, a preferred condenser is a piece of tubing, preferably between 3 centimeters and 0.1 centimeters inside diameter and between 300 centimeters and 1 centimeter long. More preferably the tube is between 1 centimeter and 0.3 centimeters in diameter and between 1 meter and 3 centimeters long.

It is presently believed that there are trade offs in optimizing the operating pressure, condenser geometry, and condenser temperature(s). Generally it is desirable to minimize analyte dilution from both con-condensable gas and residual solvent vapor, and to minimize analyte loss due to aerosol particle diffusion to condenser walls, sample transfer line walls and poor adhesion to the optical disk. It is also desirable to minimize the deposition spot area on the disk since this maximizes thickness and detection sensitivity. The design and operational tradeoffs to achieve these result in compromises. The following theoretical discussion is intended to convey the present understanding of the inventors, and the accuracy of theoretical mechanisms of operation should not be used to limit the scope or validity of the invention claims. The atomized particles are held in suspension by the gas viscosity, which is roughly independent of aerosol particle size until the particle size decreases to the order of magnitude of the mean free path of the gas molecules. This transition from what is commonly called the continuum flow regime to the molecular flow regime results in significantly less viscous drag on, and much more rapid diffusion of, the particles resulting in increased losses to the passageway surfaces. A practical lower operating pressure limit is set by the need to maintain the particles in suspension as they travel through the system. This lower pressure limit depends on the duration the particles need to held in suspension, and the particle size. For the instant apparatus the lower pressure limit is the order of magnitude of 0.1 atmospheres and 0.5 atmospheres is preferable for dried particles of about 0.01 microns, which is speculated to be the approximate size of particle generated by the pure thermal nebulizer with LC effluents approaching the current system's detection threshold. The partial pressure of residual solvent vapor leaving the last condenser is set by the temperature to which vapor equilibrated with condensate. The colder this temperature is, the less remaining solvent. A desirable operating pressure for LC eluent droplets nebulized by a pure thermal nebulizer is preferably between 0.1 and 2 atmospheres pressure, and more preferably between 0.3 and 1 atmosphere pressure. Using a colder condenser also desirably reduces the residual solvent vapor, but if the trap is below the freezing point of the solvent, volume must be supplied to store the frozen solvent. Therefore it is desirable to remove the bulk of the solvent as liquid drained to a location or locations outside the flow path. It is also desirable to minimize the volume of the cyclone, condenser and transfer lines as this minimizes residence time and chromatographic band spreading. Minimizing the total path length from the first-stage condenser to the optical disk minimizes drop out of aerosol particles.

Figure 8:
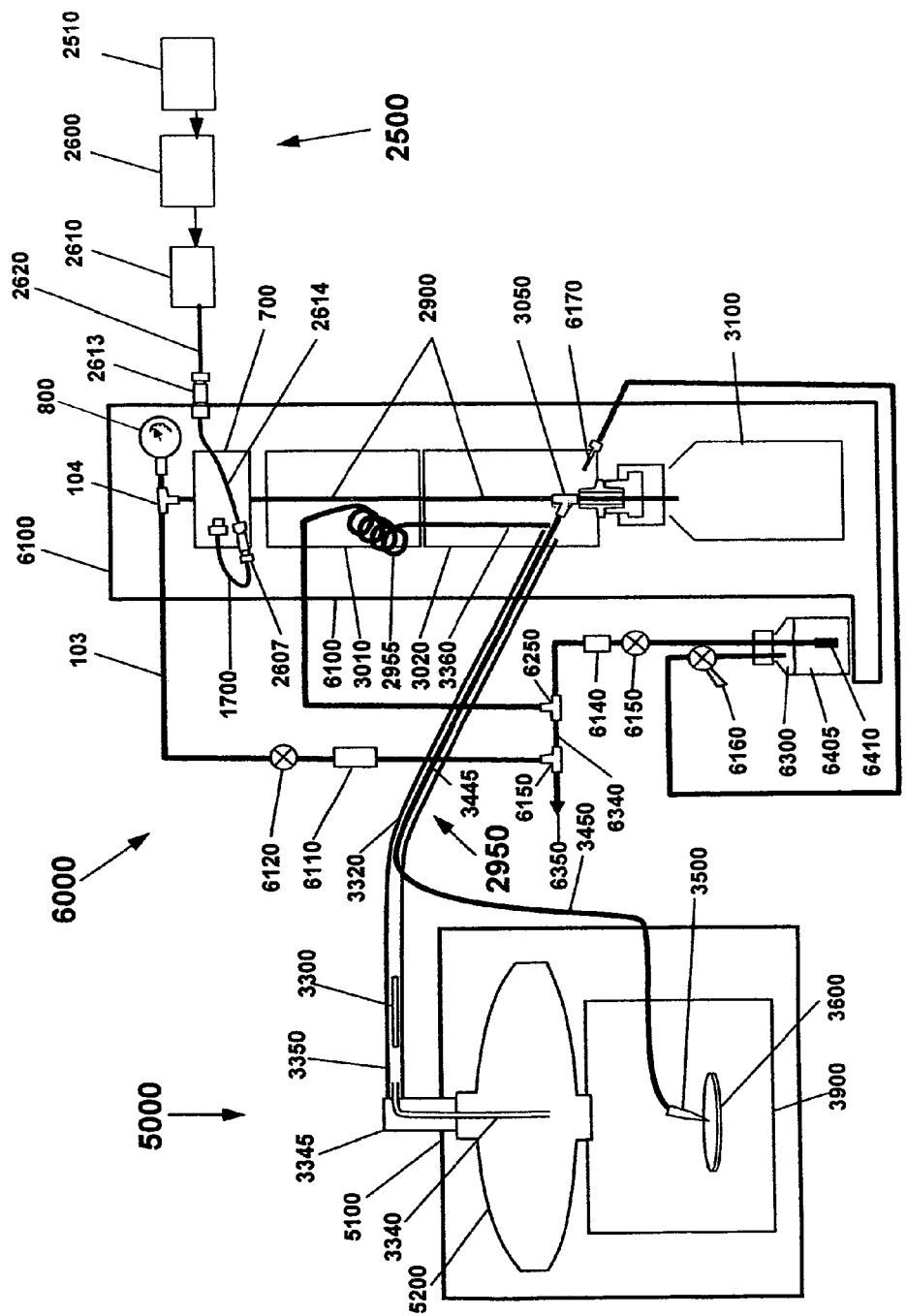
FIG. 8 is a schematic illustration of a two-stage condenser unit apparatus according to another embodiment of the present invention suitable for desolvating a Liquid Chromatograph (LC) stream followed by deposition of solute on an optical disk suitable for infrared detection.
Figure 9A:
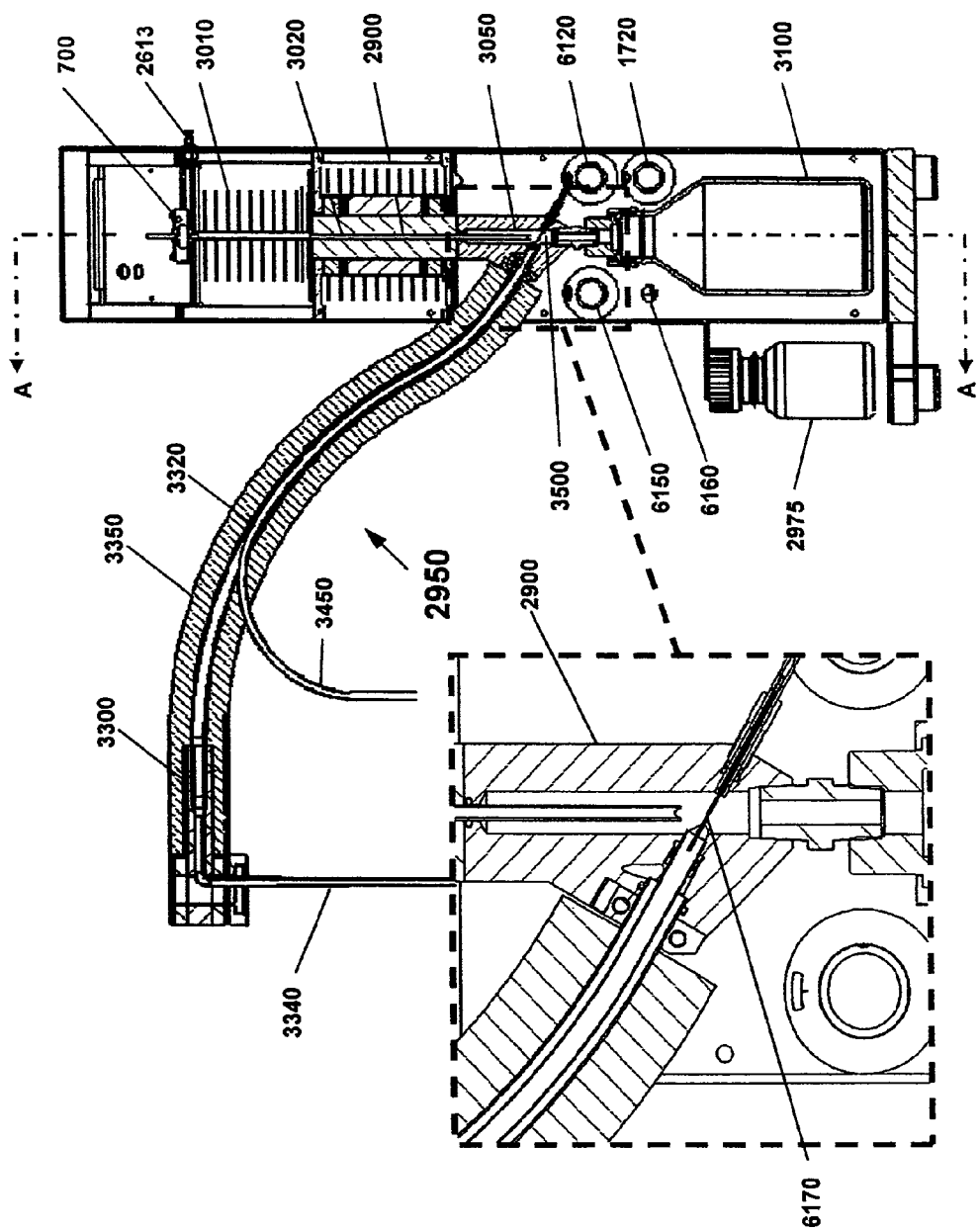
FIG. 9A is an enlarged schematic cross-sectional illustration of a portion of the apparatus shown in FIG. 8 as viewed from the front direction.
Figure 9B:
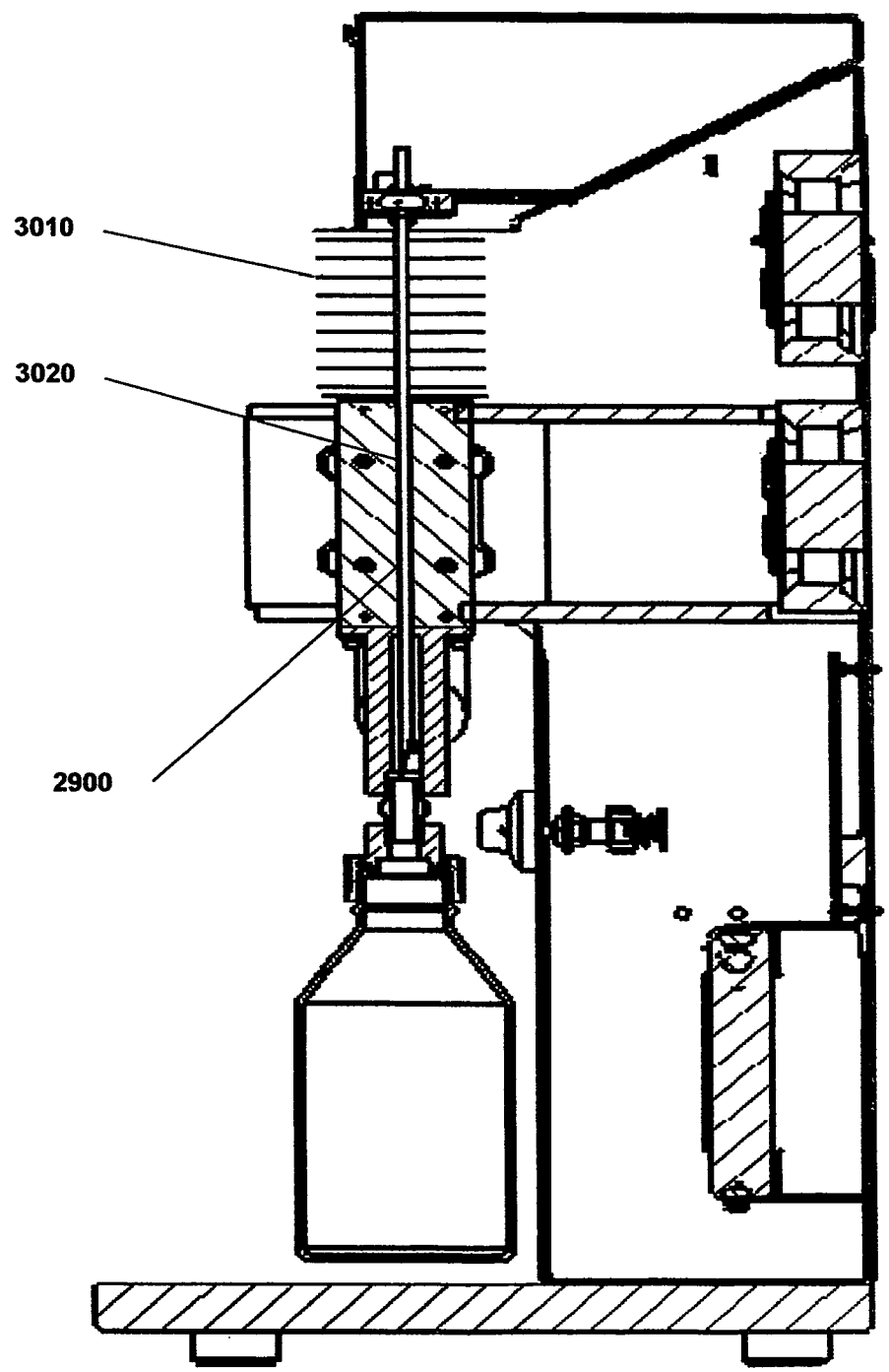
FIG. 9B is an orthogonal section viewed from the right side of FIG. 9A along the vertical plane A-A through the axis of the first-stage condenser.
Figure 10:
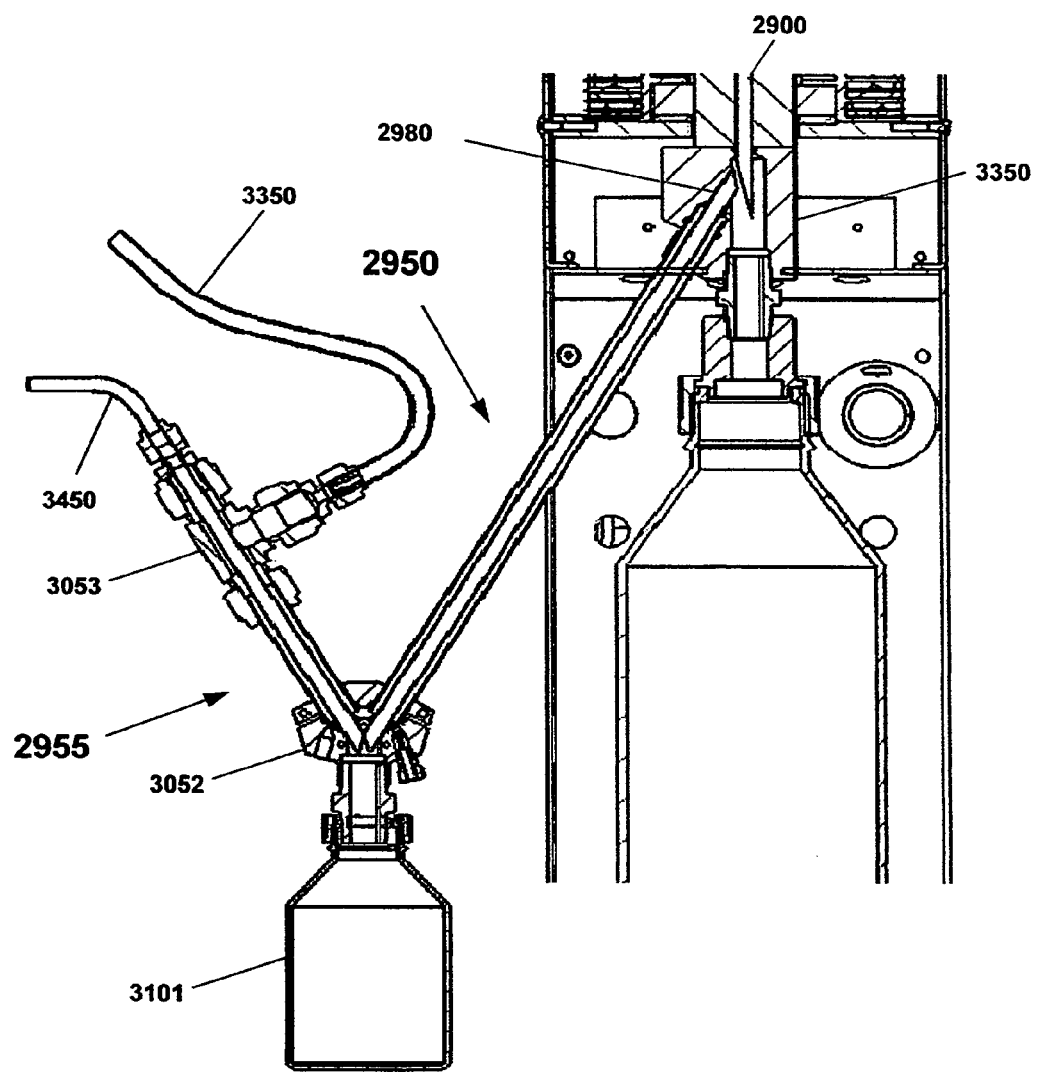
FIG. 10 is a schematic partial cross-sectional illustration of a section of an alternative multi-stage condenser system according to another embodiment of the present invention.
Figure 11A:
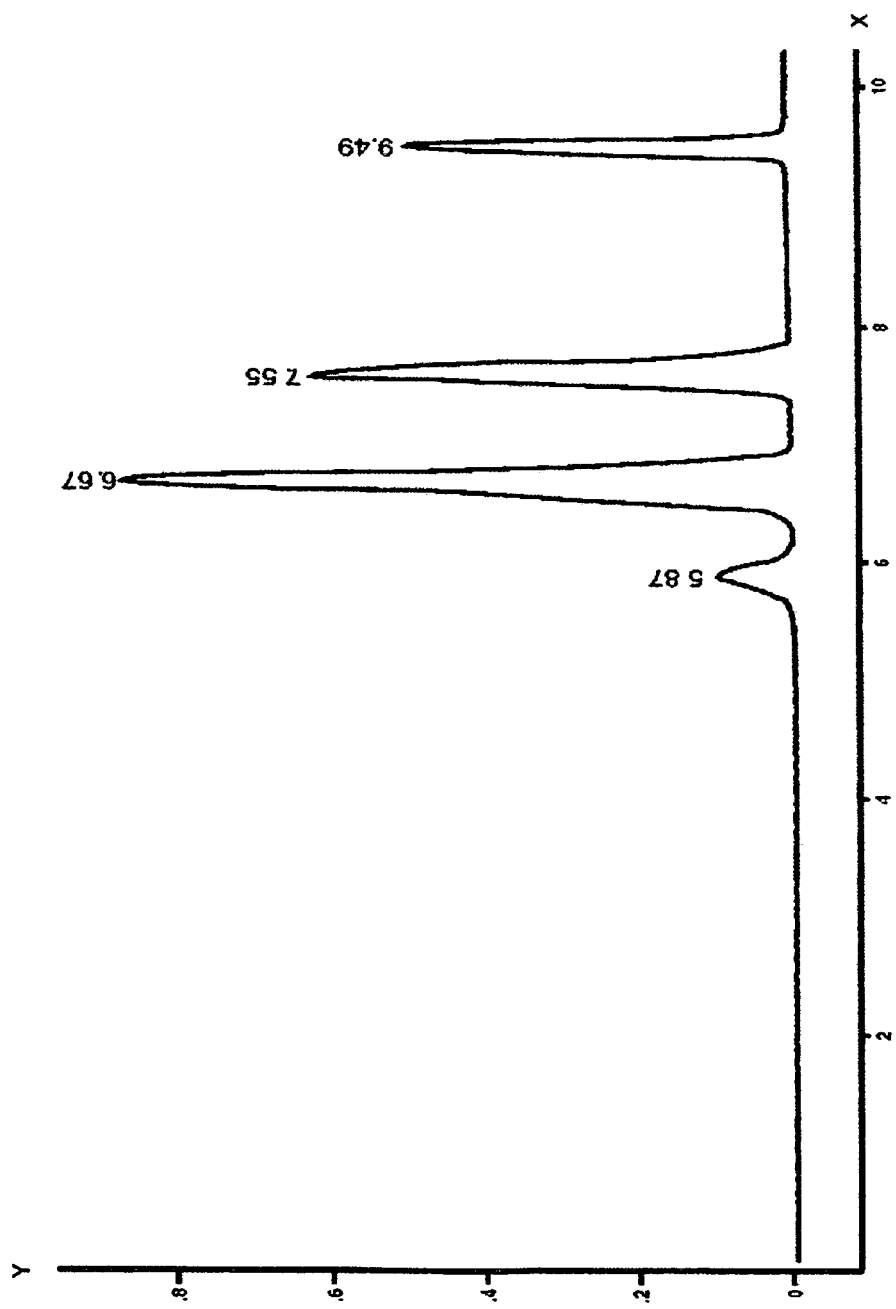
FIG. 11A shows a chromatogram produced using an apparatus as shown in FIG. 7.
Figure 11B:
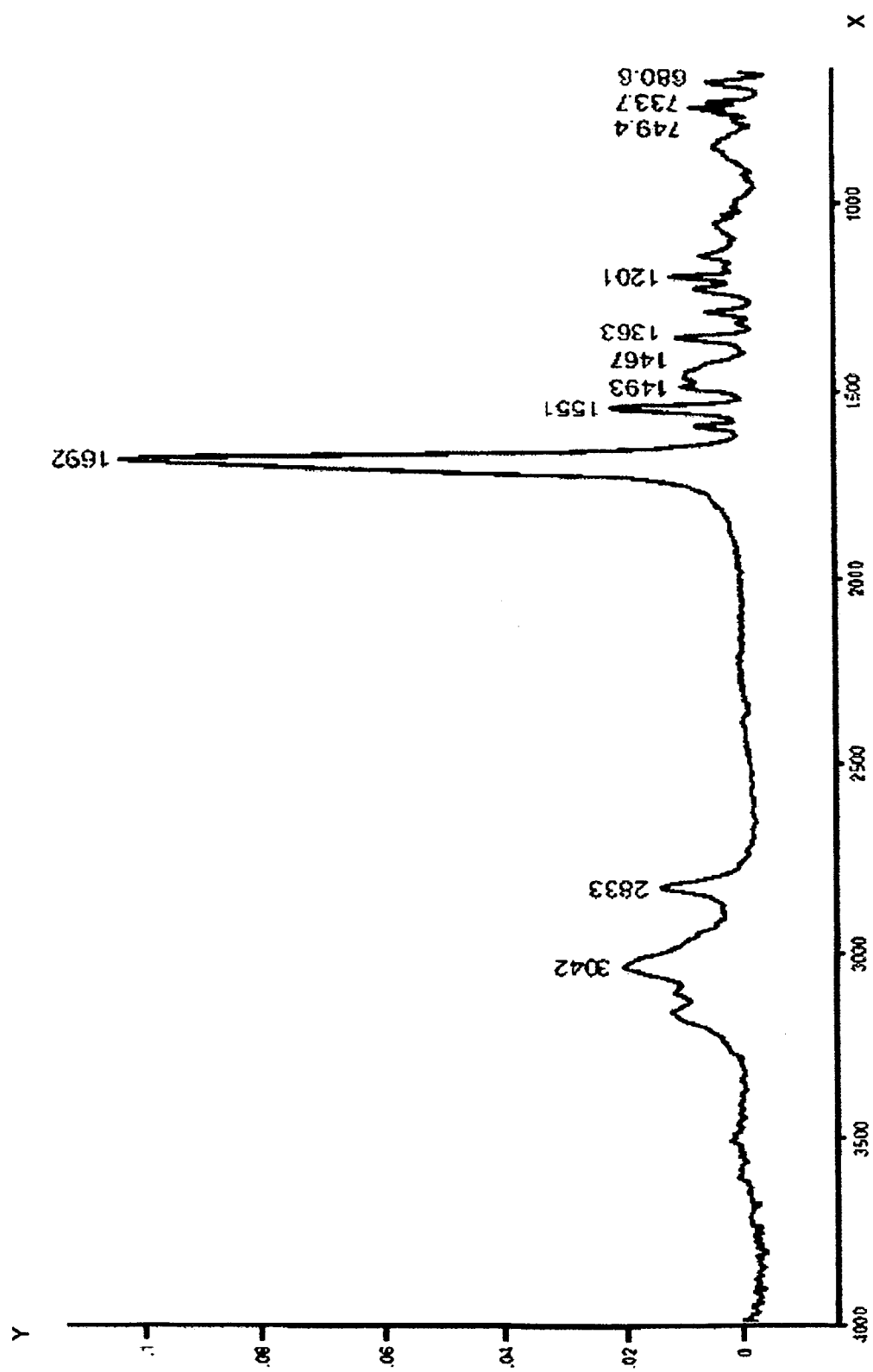
FIG. 11B shows a spectra produced using an apparatus as shown in FIG. 7.
Figure 12:
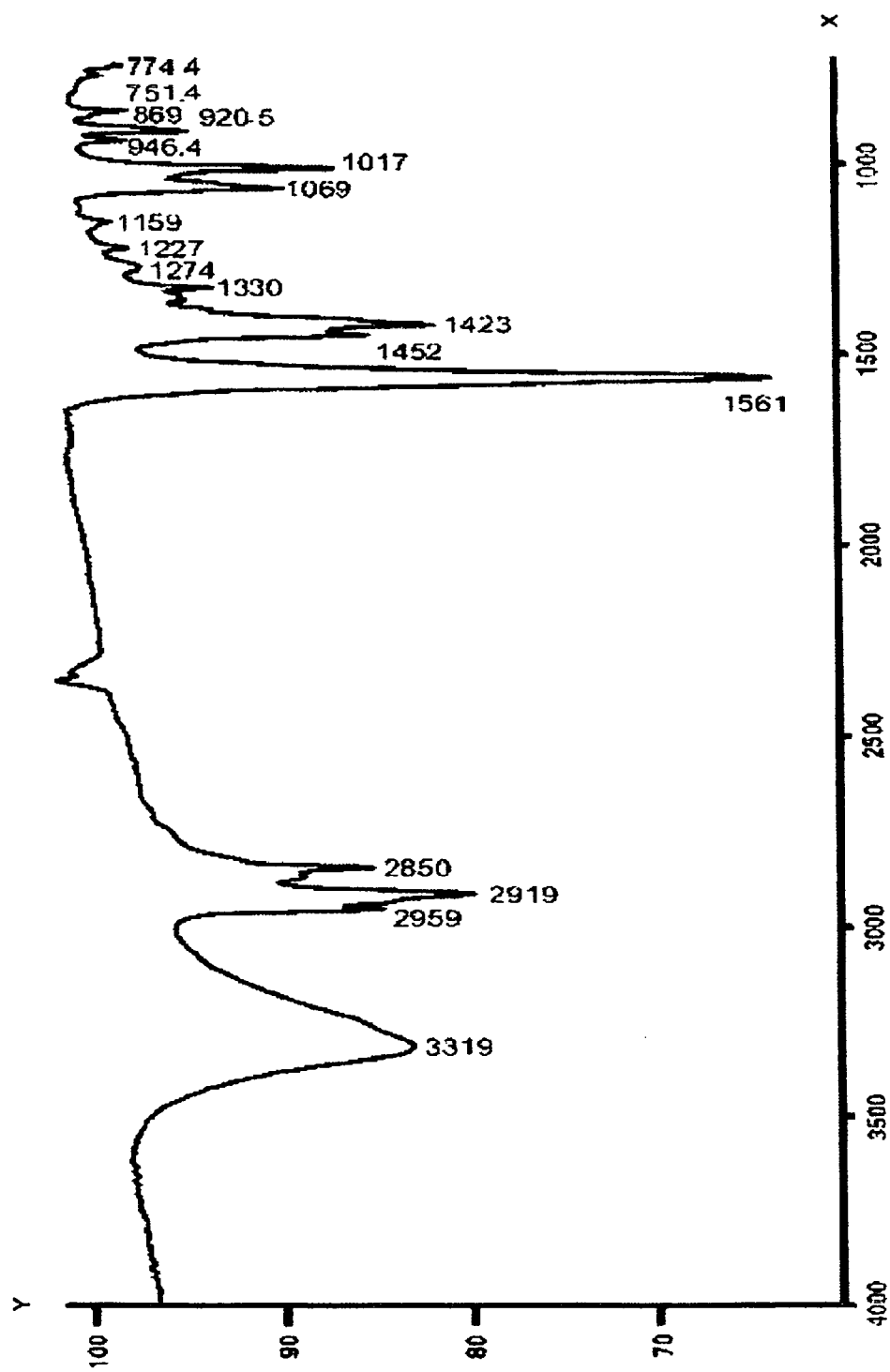
FIG. 12 shows a spectrum of a thermally labile compound produced using an apparatus as shown in FIG. 8.

For mixed solvent and gradient operation, a multi-stage liquid condenser can desirably be used. FIG. 8 and FIG. 9 show a two-stage condenser that can be used with the present invention; and FIG. 10 shows a three stage condenser that can be used with the present invention. The multi-stage condenser is preferably designed such that substantially all of the condensate from an earlier condenser stage is removed before the aerosol flow stream enters the next condenser stage. This second-stage liquid condenser 2950 can be operated at a significantly lower temperature than the first-stage condenser 2900 without plugging with frozen solvent. This is because a multi component solvent composition entering the second-stage is much lower in mass and has a lower freezing point than the condensate from the first liquid condensation stage. This lower freezing point comes from the first-stage more efficiently removing the higher freezing point, lower vapor pressure solvents leaving the vapor stream enriched in the higher vapor pressure, lower freezing point solvents. The solvent vapor composition entering the second-stage is richer in the lower freezing point solvent components, so it can operate colder without freezing its condensate. The total mass of solvent vapor entering the second-stage is dramatically reduced, with the greatest reduction in the highest freezing point solvents. Water vapor mass is typically reduced by greater than 100 fold before entering the second-stage condenser while methanol, acetonitrile and other lower freezing point solvents have less reduction. Because of the great reduction in mass flow rate of high freezing pint solvents, when operated with time varying solvent composition (gradient LC) it is possible to allow temporary freezing so long as the second-stage condenser can store the solid with out substantially blocking the flow of suspended solute before the condensed phase is again liquid. If the high freezing point solvent composition is maintained for a significant duration, other steps must be taken to prevent solvent ice or frost from blocking the passageway. While it is possible to time vary the temperature of the second-age condenser to control the build up of frozen solvent, this is undesirable because it is complicated and when warm, it allows significant solvent vapor to remain with the sample.

A preferred technique (FIG. 8 and FIG. 9) is to add a freezing point depressant solvent vapor 6300 after the first-stage condenser and before or in the second-stage condenser 2950. This second-stage condenser can drain into the same solvent collection container 3100 as the first-stage as long as the second-stage condenser 2950 sample flow is continuously up hill (FIG. 8 and FIG. 9). By flowing continuously up hill, the condensate return drain path is continuously down hill for the entire region of cooling. The amount of freezing point depressant needed is typically 1-5% of the original solvent, or a few ml liquid per hour for an LC flow rate of 1 ml/minute.

FIG. 10 shows a second-stage condenser 2950 whose condensate flows down hill and drains into a second waste bottle. In this example a third stage condenser 2955 flows uphill after the second waste bottle. This third stage can be operated with either a liquid or solid condensate.

In FIGS. 7, 8, 9 and 10 the second-stage condensers are cooled by a counter flow of cold nitrogen gas. In a preferred embodiment, this cold nitrogen gas comes from liquid nitrogen that is boiled to cool the optical disk that the sample is deposited on for FTIR analysis. The second-stage condenser temperature is regulated by temperature sensor 3320 controlling nitrogen gas heater 3330.

Methanol is a good freezing point depressant solvent. Other material potentially useful as freezing point depressant solvents in the present invention include other alcohols, acetonitrile an other materials which are mutually miscible with all the mobile phase solvents. For water containing gradients, the methanol can lower the condensate freezing point of water from 0 Celsius to less than −90 Celsius. This allows the second-stage condenser to operate much colder without risk of freezing, thereby greatly reducing the residual solvent vapor pressure and mass of residual solvent that accompanies the sample. The equilibrium vapor pressure of water at its freezing point of 0 Celsius is over 4 Torr while the vapor pressure of methanol at its freezing point of −98 Celsius is much less than 1 Torr. Any residual methanol can be readily evaporated or sublimed from the cold optical disk that the sample is deposited on at a much lower temperature than water ice can be sublimed at This allows a much colder optical sample disk that allows better capture, particularly of samples that are liquid at room temperature.

A convenient way to control the freezing point depressant vapor addition is to sparge a carrier gas such as dry nitrogen through it at the reduced pressure of the condenser. Regulating the flow of its carrier gas regulates the freezing point depressant vapor addition. Better regulation of flow, and less dilution with carrier gas can be achieved by typically elevated temperature regulation of the freezing point depressant bottle and flow path.

Deposition/Application Step (50):

In step (50), the concentrated particle stream is now ready for use in a variety of applications. This stage can be a direct detection on a measurement surface 3600, processing of the desolvated particle stream followed by detection, or collection of the particle stream for other use. A preferred embodiment is deposition of the particulates onto a controlled temperature cryogenic window, preferably under vacuum conditions, followed by examination using infrared spectroscopy or Raman spectroscopy. In this embodiment sensitivity can be increased by maximizing the deposit thickness and using microscope optics for examination The aerosol suspension is sucked through a nozzle 3500 that focuses the dried droplets into a narrow high-speed beam. An optical surface is placed under the beam to collect the solute. The deposition surface is typically in a vacuum chamber 3900 evacuated by roughing pump 4600. The deposition surface is typically temperature controlled to freeze or condense liquid solutes while avoiding significant condensation of residual solvent vapor, and desirably allowing sublimation of any residual solvent which did condense. The optical surface is then moved into the focus of the infrared microscope beam for analysis.

Another preferred embodiment is deposition of the particulates on a surface with the addition of a matrix material, either into the original liquid stream, into the particulate stream, or on the deposition surface. This matrix material can be to assist the transmission of trace quantities of analytes for FTIR, or to add compounds essential to the subsequent use. An example of the latter is deposition onto the surface, followed by analysis of the deposit by Matrix Assisted Laser Desorption Ionization using a time of flight mass spectrometer for detection. Another preferred embodiment is direct transmission of the particle stream into a mass spectrometer for analysis. Another preferred embodiment is conversion of the particulate stream into a gas stream through reaction or pyrolysis, and thence directing the stream into a gas detector, such as an ion mobility detector or a detector commonly used for gas chromatography. In another embodiment, the dried aerosol may be collected for off line use.

Although the foregoing description of this invention has been by reference to particular process steps using particular apparatus components, it will be understood by those of ordinary skill in the art that these illustrative embodiments can be readily modified in a variety of ways to adapt this invention to treat different flowing liquids under different conditions, and each of such modifications is considered to be within the scope of this invention.

The invention claimed is:

1. A solute-concentrator apparatus for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said apparatus comprising in combination:
  (a) a chamber having a chamber cavity of generally circular cross section along a chamber axis, said chamber cavity defined in part by a cavity side wall;
  (b) a source of heat for the cavity side wall that is located outside the chamber cavity in combination with a cavity side wall heat controller set to establish and maintain a solute-concentrator operating temperature, said solute-concentrator operating temperature being a temperature that is at least 20° C. greater than the boiling point of the liquid/solvent component of the flowing fluid stream at the operating pressure inside the chamber cavity, whereby vaporization of the liquid/solvent component creates a gas layer adjacent the heated cavity side wall that substantially prevents aerosol droplet contact with the cavity side wall while a substantial portion of at least one of the solute components is not vaporized;
  (c) a chamber inlet extending from outside the chamber into the chamber cavity;
  (d) one or more chamber outlets extending from the chamber cavity to outside the chamber; and,
  (e) a fluid vortical direction imparting element in or associated with said chamber cavity, the vortical element acting to impart a rotational direction to a fluid stream and selected from the group consisting of:
    (i) a fluid inlet that directs the fluid stream so as to have a net tangential component relative to the cavity side wall;
    (ii) a rotating element in said chamber cavity on which the fluid stream impinges and at least a portion of which fluid stream is thereby directed outwards toward the cavity side wall with a net circumferential directional component;
    (iii) a source of moving gas in said chamber cavity that provides moving gas directed so as to impart motion having a net circumferential component to the fluid stream; and,
    (iv) a rotational device that rotates the chamber cavity.

2. An apparatus according to claim 1 wherein the source of heat that heats the cavity side wall is selected from the group consisting of:
  (i) an electric resistance heater;
  (ii) an electric cartridge heater;
  (iii) a surface mounted electric resistance heater;
  (iv) a deposited film electrically conductive resistance heater;
  (v) an electrically conductive heater deposited on the cavity side wall;
  (vi) a radio frequency electrical induction heater;
  (vii) a microwave heater;
  (viii) a flame;
  (ix) an infrared radiant heater;
  (x) a high temperature gas; and, (xi) a high temperature liquid.

3. An apparatus according to claim 1 wherein said fluid vortical direction imparting element is capable of causing aerosol droplets of solvent and solute to rotate within the chamber cavity at a sufficient velocity to maintain larger droplets traveling substantially circumferentially adjacent said cavity side wall until the droplets have evaporated to a sufficiently small size due to solvent evaporation for drag forces to exceed centrifugal forces causing those droplets to exit the chamber cavity.

4. An apparatus according to claim 1 wherein said source of heat heats the cavity side wall to a temperature high enough to establish and maintain film boiling of aerosol droplets of solvent and solute adjacent said cavity side wall.

5. An apparatus according to claim 1 wherein at least one of the chamber outlets is located such that a product stream leaving the chamber through that chamber outlet passes through a chamber cavity region that is closer to the chamber axis than to the cavity side wall.

6. An apparatus according to claim 1 wherein the chamber forms a sealed enclosure capable of operating at a pressure different than the surrounding environment.

7. An apparatus according to claim 1 wherein film boiling prevents aerosol droplets of solvent and solute from contacting the cavity side wall and the apparatus operates without leaving any substantial portion of the solute component on the cavity side wall.

8. An apparatus according to claim 1 further comprising the flowing fluid stream in said chamber cavity wherein at least a portion of the aerosol droplets include dispersed, suspended or dissolved solids.

9. An apparatus according to claim 1 having a structure and temperature control setting whereby a portion of a fluid stream that is flowed into the chamber cavity through a chamber inlet flows out of the chamber cavity through a chamber outlet as a solid and/or liquid product portion comprising concentrated solute droplets and/or substantially dry solute particles, and that product portion flowing out of the chamber cavity has a concentration of solute in the concentrated solute droplets and/or the substantially dry solute particles that is at least ten times the concentration of solute in the fluid stream flowing into the chamber cavity.

10. An apparatus according to claim 1 wherein the inlet velocity of the flowing fluid stream in combination with the orientation of the chamber inlet contribute to rotational movement of the fluid stream inside the chamber cavity.

11. An apparatus according to claim 1 further comprising a liquid chromatograph and a connection that connects an outlet of the liquid chromatograph to a chamber inlet.

12. An apparatus according to claim 1 further comprising an analytical instrument and a connection that connects concentrated solute droplets and/or substantially dry solute particles coming from a chamber outlet directly or via another treatment component to the analytical instrument, wherein the analytical instrument is selected from a light scattering detector, an optical absorbance analyzer, an infrared spectrometer, a mass spectrometer, a nuclear magnetic resonance spectrometer, an atomic emission spectrometer, an atomic absorbance spectrometer and a flame ionization detector.

13. An apparatus according to claim 1 further comprising:
  (aa) a small diameter, very thin-walled capillary tube comprising an electrically conductive material, said tube having a capillary tube fluid entrance end and a capillary tube fluid discharge end;
  (bb) a source of heat for heating the capillary tube in combination with a capillary tube heat controller that can establish and maintain a solute-concentrator operating temperature, said source of heat comprising an electric current source and electrical connections between the current source and the respective ends of the capillary tube for passing electrical current through the capillary tube, such that a fluid stream passing from the capillary tube entrance end to the capillary tube discharge end is heated by exposure to the solute-concentrator operating temperature along at least a part of said capillary tube that is at least 20° C. above the boiling point of the liquid/solvent component of a fluid stream that comprises at least a liquid/solvent component and intermittently at least a solute component at the pressure of the capillary tube discharge end; and,
  (cc) a connection connecting the capillary tube fluid discharge end with a chamber inlet.

14. An apparatus according to claim 13 further comprising an electrical resistance measuring device connected between the respective ends of the capillary tube for generating an output to assess the sufficiency of the heat supplied to the capillary tube.

15. An apparatus according to claim 14 wherein the capillary tube heat controller is electrically connected to the electrical resistance measuring device, whereby the capillary tube heat controller regulates the electrical supply from the electric current source in accordance with the output generated by the electrical resistance measuring device in order to maintain the capillary tube at a sufficiently high average temperature along its length to produce a nebulized steam at the capillary tube discharge end.

16. An apparatus according to claim 13 wherein the capillary tube has a length of about 1 to 20 cm and an inside diameter of about 0.05 to 0.2 mm.

17. An apparatus according to claim 13 further comprising an electric power control mechanism which senses a need for a change in the electric power being delivered to the capillary tube and substantially effects such an adjustment in a time of 100 milliseconds or less.

18. An apparatus according to claim 13 further comprising:
  (dd) a condenser region defined by a condenser fluid entrance, a condenser discharge end, and a condenser flow path between the condenser fluid entrance and the condenser discharge end, said condenser flow path including at least a condenser surface;
  (ee) a cooling source that cools a fluid stream flowing along the condenser flow path, said cooling source being sufficient to cool the fluid stream to a temperature below the condensation temperature of a condensable gas component of the fluid stream prior to reaching the condenser discharge end;
  (ff) a first connection region connecting the capillary tube discharge end with an evaporation chamber inlet; and,
  (gg) a connection connecting a chamber outlet with the condenser fluid entrance.

19. An apparatus according to claim 1 further comprising:
  (aa) a condenser region defined by a condenser fluid entrance, a condenser discharge end, and a condenser flow path between the condenser fluid entrance and the condenser discharge end, said condenser flow path including at least a condenser surface;
  (bb) a cooling source that cools a fluid stream flowing along the condenser flow path, said cooling source being sufficient to cool the fluid stream to a temperature below the condensation temperature of a condensable gas component of the fluid stream prior to reaching the condenser discharge end; and,
  (cc) a connection connecting a chamber outlet with the condenser fluid entrance.

20. An apparatus according to claim 19 wherein said condenser surface is cooled to condense the condensable gas component.

21. An apparatus according to claim 19 wherein said condenser region comprises the interior of a condenser tube, the outside of which is in direct or indirect contact with a cooling fluid at a temperature low enough to provide the required cooling effect.

22. An apparatus according to claim 19 wherein said source of providing cooling comprises air cooling followed by Peltier cooling.

23. An apparatus according to claim 1 further comprising: (i) a source of droplets comprising at least a liquid/solvent component and intermittently at least a solute component which is different from the liquid/solvent component; and (ii) a connection connecting the source of droplets with a chamber inlet so as to direct the droplets into the chamber cavity.

24. An apparatus according to claim 23 wherein at least a solute component is a relatively lower-volatility solid that is dispersed, suspended or dissolved in the relatively higher-volatility liquid component.

25. An apparatus according to claim 23 wherein at least a solute component is a relatively lower-volatility liquid that is dispersed, suspended or dissolved in the relatively higher-volatility liquid component.

26. A solute-concentrator system for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said system comprising in combination:

(a) a chamber having a chamber cavity of generally circular cross section along a chamber axis, said chamber cavity defined in part by a cavity side wall;

(b) a source of heat for the cavity side wall that is located outside the chamber cavity in combination with a cavity side wall heat controller set to establish and maintain a solute-concentrator operating temperature, said solute-concentrator operating temperature being a temperature that is at least 20° C. greater than the boiling point of the liquid/solvent component of the flowing fluid stream at the operating pressure inside the chamber cavity, whereby vaporization of the liquid/solvent component creates a gas layer adjacent the heated cavity side wall that substantially prevents aerosol droplet contact with the cavity side wall while a substantial portion of at least one of the solute components is not vaporized;

(c) a chamber inlet extending from outside the chamber into the chamber cavity;

(d) one or more chamber outlets extending from the chamber cavity to outside the chamber;

(e) a fluid vortical direction imparting element in or associated with said chamber cavity, the vortical element acting to impart a rotational direction to a fluid stream and selected from the group consisting of:

(i) a fluid inlet that directs the fluid stream so as to have a net tangential component relative to the cavity side wall;

(ii) a rotating element in said chamber cavity on which the fluid stream impinges and at least a portion of which fluid stream is thereby directed outwards toward the cavity side wall with a net circumferential directional component;

(iii) a source of moving gas in said chamber cavity that provides moving gas directed so as to impart motion having a net circumferential component to the fluid stream; and, (iv) a rotational device that rotates the chamber cavity;

(f) a fluid stream in at least the chamber inlet, the fluid stream comprising a predominant portion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in the liquid/solvent component;

(g) the cavity side wall is established at a temperature that is at least 20° C. greater than the boiling point of the liquid/solvent component of the aerosol droplets whereby a gas layer of vaporized solvent between a droplet and the heated cavity side wall substantially prevents aerosol droplet contact with the cavity side wall while a substantial portion of at least one of the solute components is not vaporized; and, (h) a concentrated product portion comprising concentrated solute droplets and/or substantially dry solute particles at a chamber outlet in which the concentration of solute in the concentrated solute droplets and/or the substantially dry solute particles is significantly greater than the concentration of solute in the fluid stream flowing into the chamber cavity.

27. The system of claim 26 wherein the source of heat that maintains the cavity side wall at the proper temperature is a heating element selected from the group consisting of: (i) an electric resistance heater; (ii) an electric cartridge heater; (iii) a surface mounted electric resistance heater; (iv) a deposited film electrically conductive resistance heater; (v) an electrically conductive heater deposited on the cylindrical-shaped surface; (vi) a radio frequency electrical induction heater; (vii) a microwave heater; (viii) a flame; (ix) an infrared radiant heater; (x) a high temperature gas; and, (xi) a high temperature liquid.

28. The system of claim 26 wherein the fluid vortical direction imparting element causes aerosol droplets of solvent and solute to rotate within the cavity side wall at a sufficient velocity to maintain larger droplets traveling substantially circumferentially adjacent said cavity side wall until the droplets have evaporated to a sufficiently small size due to solvent evaporation for drag forces to exceed centrifugal force causing these droplets to exit the chamber cavity.

29. The system of claim 26 wherein the cavity side wall is maintained at a temperature high enough to establish and maintain film boiling of aerosol droplets containing solvent and solute adjacent the cavity side wall.

30. The system of claim 26 further wherein there is a product portion with an elevated concentration of solute leaving a chamber outlet through an outlet that is closer to an axis of the chamber than it is to the cavity side wall.

31. The system of claim 26 wherein there is a product portion comprising concentrated solute droplets and/or substantially dry solute particles exiting a chamber outlet with a concentration of solute in the concentrated solute droplets and/or the substantially dry solute particles that is at least ten times the concentration of solute in the fluid stream flowing into the chamber cavity.

32. The system of claim 26 further comprising a liquid chromatograph having an outlet in fluid communication with the chamber inlet.

33. The system of claim 26 further comprising a product analysis apparatus selected from a light scattering detector, optical absorbance analyzer, infrared spectrometer, mass spectrometer, nuclear magnetic resonance spectrometer, atomic emission spectrometer, atomic absorbance spectrometer or flame ionization detector and a fluid connection between a chamber outlet and the product analysis apparatus.

34. A system according to claim 26 further comprising a small diameter, very thin-walled capillary tube comprising an electrically conductive material, the capillary tube being heated by passing an electric current through the capillary tube sufficient to heat a fluid stream inside the capillary tube to a temperature that is at least 20° C. above the boiling point of the liquid component of the fluid stream at the pressure of the capillary tube discharge end before it reaches the capillary tube discharge end of the capillary tube to create a nebulized stream, wherein the discharge end of the capillary tube is in fluid communication with the chamber inlet.

35. The system according to claim 34 further comprising a regulator for regulating the electrical power supply to the capillary tube based on a measurement of the electrical resistance of the capillary tube.

36. A solute-concentrator apparatus for evaporating liquid from a flowing fluid stream that comprises a predominant proportion of a liquid/solvent component and at least intermittently minor proportions of one or more liquid and/or solid solute components which is/are different from the liquid/ solvent component and which have a low volatility relative to the liquid/solvent component, said solute component(s) being dispersed, suspended or dissolved in aerosol droplets of the liquid/solvent component, said apparatus comprising in combination:
(a) a chamber having a chamber cavity of generally circular cross section along a chamber axis, said chamber cavity defined in part by a cavity side wall;
(b) a source of heat for the cavity side wall that is located outside the chamber cavity in combination with a cavity side wall heat controller set to establish and maintain a solute-concentrator operating temperature, said solute-concentrator operating temperature being a temperature that is at least 20° C. greater than the boiling point of the liquid/solvent component of the flowing fluid stream at the operating pressure inside the chamber cavity, whereby vaporization of the liquid/solvent component creates a gas layer adjacent the heated cavity side wall that substantially prevents aerosol droplet contact with the cavity side wall while a substantial portion of at least one of the solute components is not vaporized;
(c) a chamber inlet extending from outside the chamber into the chamber cavity;
(d) one or more chamber outlets extending from the chamber cavity to outside the chamber; and,
(e) a fluid vortical direction imparting element in or associated with said chamber cavity, the vortical element acting to impart a rotational direction to a fluid stream and selected from the group consisting of:
(i) a fluid inlet that directs the fluid stream so as to have a net tangential component relative to the cavity side wall;
(ii) a rotating element in said chamber cavity on which the fluid stream impinges and at least a portion of which fluid stream is thereby directed outwards toward the cavity side wall with a net circumferential directional component; and, (iii) a rotational device that rotates the chamber cavity.

37. A solute-concentrator system for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said system comprising in combination:
(a) a chamber having a chamber cavity of generally circular cross section along a chamber axis, said chamber cavity defined in part by a cavity side wall;
(b) a source of heat for the cavity side wall that is located outside the chamber cavity in combination with a cavity side wall heat controller set to establish and maintain a solute-concentrator operating temperature, said solute-concentrator operating temperature being a temperature that is at least 20° C. greater than the boiling point of the liquid/solvent component of the flowing fluid stream at the operating pressure inside the chamber cavity, whereby vaporization of the liquid/solvent component creates a gas layer adjacent the heated cavity side wall that substantially prevents aerosol droplet contact with the cavity side wall while a substantial portion of at least one of the solute components is not vaporized;
(c) a chamber inlet extending from outside the chamber into the chamber cavity;
(d) one or more chamber outlets extending from the chamber cavity to outside the chamber;
(e) a fluid vortical direction imparting element in or associated with said chamber cavity, the vortical element acting to impart a rotational direction to a fluid stream and selected from the group consisting of:
(i) a fluid inlet that directs the fluid stream so as to have a net tangential component relative to the cavity side wall;
(ii) a rotating element in said chamber cavity on which the fluid stream impinges and at least a portion of which fluid stream is thereby directed outwards toward the cavity side wall with a net circumferential directional component; and,
(iii) a rotational device that rotates the chamber cavity;
(f) a fluid stream in at least the chamber inlet, the fluid stream comprising a predominant portion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in the liquid/solvent component;
(g) the cavity side wall is established at a temperature that is at least 20° C. greater than the boiling point of the liquid/solvent component of the aerosol droplets whereby a gas layer of vaporized solvent between a droplet and the heated cavity side wall substantially prevents aerosol droplet contact with the cavity side wall while a substantial portion of at least one of the solute components is not vaporized; and,
(h) a concentrated product portion comprising concentrated solute droplets and/or substantially dry solute particles at a chamber outlet in which the concentration of solute in the concentrated solute droplets and/or the substantially dry solute particles is significantly greater than the concentration of solute in the fluid stream flowing into the chamber cavity.

38. A solute-concentrator system for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said system comprising in combination:
(a) a chamber having a chamber cavity of generally circular cross section along a chamber axis, said chamber cavity defined in part by a cavity side wall;
(b) a source of heat for the cavity side wall that is located outside the chamber cavity in combination with a cavity side wall heat controller set to establish and maintain a temperature that is between 100° C. and 400° C., whereby vaporization of the liquid/solvent component creates a gas layer adjacent the heated cavity side wall that substantially prevents aerosol droplet contact with the cavity side wall while a substantial portion of at least one of the solute components is not vaporized;
(c) a chamber inlet extending from outside the chamber into the chamber cavity;
(d) one or more chamber outlets extending from the chamber cavity to outside the chamber;
(e) a fluid vortical direction imparting element in or associated with said chamber cavity, the vortical element acting to impart a rotational direction to a fluid stream and selected from the group consisting of:

(i) a fluid inlet that directs the fluid stream so as to have a net tangential component relative to the cavity side wall;
(ii) a rotating element in said chamber cavity on which the fluid stream impinges and at least a portion of which fluid stream is thereby directed outwards toward the cavity side wall with a net circumferential directional component;

(iii) a source of moving gas in said chamber cavity that provides moving gas directed so as to impart motion having a net circumferential component to the fluid stream; and, (iv) a rotational device that rotates the chamber cavity;

(f) a fluid stream in at least the chamber inlet, the fluid stream comprising a predominant portion of a liquid/solvent component that consists essentially of organic solvents or water mixed with one or more miscible organic solvents and at least intermittently minor proportions of one or more liquid and/or solid solute components which is/are different from the liquid/solvent component and which have a low volatility relative to the liquid/solvent component, said solute component(s) being dispersed, suspended or dissolved in the liquid/solvent component;

(g) the cavity side wall is established at a temperature of between 100° C. and 400° C. whereby a gas layer of vaporized solvent between a droplet and the heated cavity side wall substantially prevents aerosol droplet contact with the cavity side wall while a substantial portion of at least one of the solute components is not vaporized; and, (h) a concentrated product portion comprising concentrated solute droplets and/or substantially dry solute particles at a chamber outlet in which the concentration of solute in the concentrated solute droplets and/or the substantially dry solute particles is significantly greater than the concentration of solute in the fluid stream flowing into the chamber cavity.

39. A solute-concentrator system for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said system comprising in combination:

(a) a chamber having a chamber cavity of generally circular cross section along a chamber axis, said chamber cavity defined in part by a cavity side wall;

(b) a source of heat for the cavity side wall that is located outside the chamber cavity in combination with a cavity side wall heat controller set to establish and maintain a temperature that is at least 150° C., whereby vaporization of the liquid/solvent component creates a gas layer adjacent the heated cavity side wall that substantially prevents aerosol droplet contact with the cavity side wall while a substantial portion of at least one of the solute components is not vaporized;

(c) a chamber inlet extending from outside the chamber into the chamber cavity;

(d) one or more chamber outlets extending from the chamber cavity to outside the chamber;

(e) a fluid vortical direction imparting element in or associated with said chamber cavity, the vortical element acting to impart a rotational direction to a fluid stream and selected from the group consisting of:

(i) a fluid inlet that directs the fluid stream so as to have a net tangential component relative to the cavity side wall;

(ii) a rotating element in said chamber cavity on which the fluid stream impinges and at least a portion of which fluid stream is thereby directed outwards toward the cavity side wall with a net circumferential directional component;

(iii) a source of moving gas in said chamber cavity that provides moving gas directed so as to impart motion having a net circumferential component to the fluid stream; and, (iv) a rotational device that rotates the chamber cavity;

(f) a fluid stream in at least the chamber inlet, the fluid stream comprising a predominant portion of a liquid/solvent component that consists essentially of organic solvents or water mixed with one or more miscible organic solvents and at least intermittently minor proportions of one or more liquid and/or solid solute components which is/are different from the liquid/solvent component and which have a low volatility relative to the liquid/solvent component, said solute component(s) being dispersed, suspended or dissolved in the liquid/solvent component;

(g) the cavity side wall is established at a temperature of at least 150° C. whereby a gas layer of vaporized solvent between a droplet and the heated cavity side wall substantially prevents aerosol droplet contact with the cavity side wall while a substantial portion of at least one of the solute components is not vaporized; and, (h) a concentrated product portion comprising concentrated solute droplets and/or substantially dry solute particles at a chamber outlet in which the concentration of solute in the concentrated solute droplets and/or the substantially dry solute particles is significantly greater than the concentration of solute in the fluid stream flowing into the chamber cavity.

40. A solute-concentrator system for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said system comprising in combination:

(a) a chamber operated below atmospheric pressure and having a chamber cavity of generally circular cross section along a chamber axis, said chamber cavity defined in part by a cavity side wall;

(b) a source of heat for the cavity side wall that is located outside the chamber cavity in combination with a cavity side wall heat controller set to establish and maintain a temperature that is between 150° C. and 250° C., whereby vaporization of the liquid/solvent component creates a gas layer adjacent the heated cavity side wall that substantially prevents aerosol droplet contact with the cavity side wall while a substantial portion of at least one of the solute components is not vaporized;

(c) a chamber inlet extending from outside the chamber into the chamber cavity;

(d) one or more chamber outlets extending from the chamber cavity to outside the chamber;

(e) a fluid vortical direction imparting element in or associated with said chamber cavity, the vortical element acting to impart a rotational direction to a fluid stream and selected from the group consisting of:

(i) a fluid inlet that directs the fluid stream so as to have a net tangential component relative to the cavity side wall;
(ii) a rotating element in said chamber cavity on which the fluid stream impinges and at least a portion of which fluid stream is thereby directed outwards toward the cavity side wall with a net circumferential directional component;
(iii) a source of moving gas in said chamber cavity that provides moving gas directed so as to impart motion having a net circumferential component to the fluid stream; and,
(iv) a rotational device that rotates the chamber cavity;
(f) a fluid stream in at least the chamber inlet, the fluid stream comprising a predominant portion of a liquid/solvent component that consists essentially of organic solvents or water mixed with one or more miscible organic solvents and at least intermittently minor proportions of one or more liquid and/or solid solute components which is/are different from the liquid/solvent component and which have a low volatility relative to the liquid/solvent component, said solute component(s) being dispersed, suspended or dissolved in the liquid/solvent component;
(g) the cavity side wall is established at a temperature of between 150° C. and 250° C. whereby a gas layer of vaporized solvent between a droplet and the heated cavity side wall substantially prevents aerosol droplet contact with the cavity side wall while a substantial portion of at least one of the solute components is not vaporized; and,
(h) a concentrated product portion comprising concentrated solute droplets and/or substantially dry solute particles at a chamber outlet in which the concentration of solute in the concentrated solute droplets and/or the substantially dry solute particles is significantly greater than the concentration of solute in the fluid stream flowing into the chamber cavity.

41. A solute-concentrator apparatus for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said apparatus comprising in combination:
(a) a chamber having a chamber cavity of generally circular cross section along a chamber axis, said chamber cavity defined in part by a cavity side wall;
(b) a source of heat for the cavity side wall that is located outside the chamber cavity in combination with a cavity side wall heat controller set to establish and maintain a temperature that is between 100° C. and 400° C., whereby vaporization of the liquid/solvent component creates a gas layer adjacent the heated cavity side wall that substantially prevents aerosol droplet contact with the cavity side wall while a substantial portion of at least one of the solute components is not vaporized;
(c) a chamber inlet extending from outside the chamber into the chamber cavity;
(d) one or more chamber outlets extending from the chamber cavity to outside the chamber; and,
(e) a fluid vortical direction imparting element in or associated with said chamber cavity, the vortical element acting to impart a rotational direction to a fluid stream and selected from the group consisting of:
(i) a fluid inlet that directs the fluid stream so as to have a net tangential component relative to the cavity side wall;
(ii) a rotating element in said chamber cavity on which the fluid stream impinges and at least a portion of which fluid stream is thereby directed outwards toward the cavity side wall with a net circumferential directional component; and,
(iii) a rotational device that rotates the chamber cavity.

42. An apparatus according to claim 41 wherein at least a portion of the flowing fluid stream is impacted inside the chamber cavity by a stream of solvent vapor, other liquid vapor, other gas, sample-containing liquid, other liquid, liquid droplets or a combination thereof which contribute to rotational movement of the fluid stream inside the chamber cavity.

43. A solute-concentrator apparatus for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said apparatus comprising in combination:
(a) a chamber having a chamber cavity of generally circular cross section along a chamber axis, said chamber cavity defined in part by a cavity side wall;
(b) a source of heat for the cavity side wall that is located outside the chamber cavity in combination with a cavity side wall heat controller set to establish and maintain a temperature that is at least 150° C., whereby vaporization of the liquid/solvent component creates a gas layer adjacent the heated cavity side wall that substantially prevents aerosol droplet contact with the cavity side wall while a substantial portion of at least one of the solute components is not vaporized;
(c) a chamber inlet extending from outside the chamber into the chamber cavity;
(d) one or more chamber outlets extending from the chamber cavity to outside the chamber; and,
(e) a fluid vortical direction imparting element in or associated with said chamber cavity, the vortical element acting to impart a rotational direction to a fluid stream and selected from the group consisting of:
(i) a fluid inlet that directs the fluid stream so as to have a net tangential component relative to the cavity side wall;
(ii) a rotating element in said chamber cavity on which the fluid stream impinges and at least a portion of which fluid stream is thereby directed outwards toward the cavity side wall with a net circumferential directional component; and,
(iii) a rotational device that rotates the chamber cavity.

44. A solute-concentrator apparatus for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said apparatus comprising in combination:
(a) a chamber operated below atmospheric pressure and having a chamber cavity of generally circular cross section along a chamber axis, said chamber cavity defined in part by a cavity side wall;

(b) a source of heat for the cavity side wall that is located outside the chamber cavity in combination with a cavity side wall heat controller set to establish and maintain a temperature that is between 150° C. and 250° C., whereby vaporization of the liquid/solvent component creates a gas layer adjacent the heated cavity side wall that substantially prevents aerosol droplet contact with the cavity side wall while a substantial portion of at least one of the solute components is not vaporized;

(c) a chamber inlet extending from outside the chamber into the chamber cavity;

(d) one or more chamber outlets extending from the chamber cavity to outside the chamber; and, (e) a fluid vortical direction imparting element in or associated with said chamber cavity, the vortical element acting to impart a rotational direction to a fluid stream and selected from the group consisting of:

(i) a fluid inlet that directs the fluid stream so as to have a net tangential component relative to the cavity side wall;

(ii) a rotating element in said chamber cavity on which the fluid stream impinges and at least a portion of which fluid stream is thereby directed outwards toward the cavity side wall with a net circumferential directional component; and, (iii) a rotational device that rotates the chamber cavity.

45. A solute-concentrator system for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said system comprising in combination:

(a) a chamber having a chamber cavity of generally circular cross section along a chamber axis, said chamber cavity defined in part by a cavity side wall;

(b) a source of heat for the cavity side wall that is located outside the chamber cavity in combination with a cavity side wall heat controller set to establish and maintain a temperature that is between 100° C. and 400° C., whereby vaporization of the liquid/solvent component creates a gas layer adjacent the heated cavity side wall that substantially prevents aerosol droplet contact with the cavity side wall while a substantial portion of at least one of the solute components is not vaporized;

(c) a chamber inlet extending from outside the chamber into the chamber cavity;

(d) one or more chamber outlets extending from the chamber cavity to outside the chamber;

(e) a fluid vortical direction imparting element in or associated with said chamber cavity, the vortical element acting to impart a rotational direction to a fluid stream and selected from the group consisting of:

(i) a fluid inlet that directs the fluid stream so as to have a net tangential component relative to the cavity side wall;

(ii) a rotating element in said chamber cavity on which the fluid stream impinges and at least a portion of which fluid stream is thereby directed outwards toward the cavity side wall with a net circumferential directional component; and, (iii) a rotational device that rotates the chamber cavity;

(f) a fluid stream in at least the chamber inlet, the fluid stream comprising a predominant portion of a liquid/solvent component that consists essentially of organic solvents or water mixed with one or more miscible organic solvents and at least intermittently minor proportions of one or more liquid and/or solid solute components which is/are different from the liquid/solvent component and which have a low volatility relative to the liquid/solvent component, said solute component(s) being dispersed, suspended or dissolved in the liquid/solvent component;

(g) the cavity side wall is established at a temperature of between 100° C. and 400° C. whereby a gas layer of vaporized solvent between a droplet and the heated cavity side wall substantially prevents aerosol droplet contact with the cavity side wall while a substantial portion of at least one of the solute components is not vaporized; and, (h) a concentrated product portion comprising concentrated solute droplets and/or substantially dry solute particles at a chamber outlet in which the concentration of solute in the concentrated solute droplets and/or the substantially dry solute particles is significantly greater than the concentration of solute in the fluid stream flowing into the chamber cavity.

46. A solute-concentrator system for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said system comprising in combination:

(a) a chamber having a chamber cavity of generally circular cross section along a chamber axis, said chamber cavity defined in part by a cavity side wall;

(b) a source of heat for the cavity side wall that is located outside the chamber cavity in combination with a cavity side wall heat controller set to establish and maintain a temperature that is at least 150° C., whereby vaporization of the liquid/solvent component creates a gas layer adjacent the heated cavity side wall that substantially prevents aerosol droplet contact with the cavity side wall while a substantial portion of at least one of the solute components is not vaporized;

(c) a chamber inlet extending from outside the chamber into the chamber cavity;

(d) one or more chamber outlets extending from the chamber cavity to outside the chamber;

(e) a fluid vortical direction imparting element in or associated with said chamber cavity, the vortical element acting to impart a rotational direction to a fluid stream and selected from the group consisting of:

(i) a fluid inlet that directs the fluid stream so as to have a net tangential component relative to the cavity side wall;

(ii) a rotating element in said chamber cavity on which the fluid stream impinges and at least a portion of which fluid stream is thereby directed outwards toward the cavity side wall with a net circumferential directional component; and, (iii) a rotational device that rotates the chamber cavity;

(f) a fluid stream in at least the chamber inlet, the fluid stream comprising a predominant portion of a liquid/solvent component that consists essentially of organic solvents or water mixed with one or more miscible organic solvents and at least intermittently minor proportions of one or more liquid and/or solid solute components which is/are different from the liquid/solvent component and which have a low volatility relative to the liquid/solvent component, said solute component(s) being dispersed, suspended or dissolved in the liquid/solvent component;

(g) the cavity side wall is established at a temperature of at least 150° C. whereby a gas layer of vaporized solvent between a droplet and the heated cavity side wall substantially prevents aerosol droplet contact with the cavity side wall while a substantial portion of at least one of the solute components is not vaporized; and, (h) a concentrated product portion comprising concentrated solute droplets and/or substantially dry solute particles at a chamber outlet in which the concentration of solute in the concentrated solute droplets and/or the substantially dry solute particles is significantly greater than the concentration of solute in the fluid stream flowing into the chamber cavity.

47. A solute-concentrator system for evaporating liquid from a flowing fluid stream that comprises a predominant proportion of a liquid/solvent component and at least intermittently minor proportions of one or more liquid and/or solid solute components which is/are different from the liquid/solvent component and which have a low volatility relative to the liquid/solvent component, said solute component(s) being dispersed, suspended or dissolved in aerosol droplets of the liquid/solvent component, said system comprising in combination:

(a) a chamber operated below atmospheric pressure and having a chamber cavity of generally circular cross section along a chamber axis, said chamber cavity defined in part by a cavity side wall;

(b) a source of heat for the cavity side wall that is located outside the chamber cavity in combination with a cavity side wall heat controller set to establish and maintain a temperature that is 150° C. and 250° C., whereby vaporization of the liquid/solvent component creates a gas layer adjacent the heated cavity side wall that substantially prevents aerosol droplet contact with the cavity side wall while a substantial portion of at least one of the solute components is not vaporized;

(c) a chamber inlet extending from outside the chamber into the chamber cavity;

(d) one or more chamber outlets extending from the chamber cavity to outside the chamber;

(e) a fluid vortical direction imparting element in or associated with said chamber cavity, the vortical element acting to impart a rotational direction a fluid stream and selected from the group consisting of:

(i) a fluid inlet that directs the fluid stream so as to have a net tangential component relative to the cavity side wall;

(ii) a rotating element in said chamber cavity on which the fluid stream impinges and at least a portion of which fluid stream is thereby directed outwards toward the cavity side wall with a net circumferential directional component; and, (iii) a rotational device that rotates the chamber cavity;

(f) a fluid stream in at least the chamber inlet, the fluid stream comprising a predominant portion of a liquid/solvent component that consists essentially of organic solvents or water mixed with one or more miscible organic solvents and at least intermittently minor proportions of one or more liquid and/or solid solute components which is/are different from the liquid/solvent component and which have a low volatility relative to the liquid/solvent component, said solute component(s) being dispersed, suspended or dissolved in the liquid/solvent component;

(g) the cavity side wall is established at a temperature of between 150° C. and 250° C. whereby a gas layer of vaporized solvent between a droplet and the heated cavity side wall substantially prevents aerosol droplet contact with the cavity side wall while a substantial portion of at least one of the solute components is not vaporized; and, (h) a concentrated product portion comprising concentrated solute droplets and/or substantially dry solute particles at a chamber outlet in which the concentration of solute in the concentrated solute droplets and/or the substantially dry solute particles is significantly greater than the concentration of solute in the fluid stream flowing into the chamber cavity.

\* \* \* \* \*